US006955897B2

(12) United States Patent
Wolfner et al.

(10) Patent No.: US 6,955,897 B2
(45) Date of Patent: Oct. 18, 2005

(54) GENES FOR MALE ACCESSORY GLAND PROTEINS IN *DROSOPHILA MELANOGASTER*

(75) Inventors: Mariana F. Wolfner, Ithaca, NY (US);
Oliver Lung, Ithaca, NY (US);
Khanh-Uyen Tram, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 288 days.

(21) Appl. No.: 10/114,774

(22) Filed: Apr. 2, 2002

(65) Prior Publication Data

US 2003/0166533 A1 Sep. 4, 2003

Related U.S. Application Data

(62) Division of application No. 09/219,983, filed on Dec. 23, 1998, now Pat. No. 6,380,159.
(60) Provisional application No. 60/071,315, filed on Dec. 23, 1997.

(51) Int. Cl.$^7$ .......................... C12P 21/06; C07H 17/00; C07K 14/00
(52) U.S. Cl. ................ 435/69.1; 435/320.1; 435/252.2; 435/325; 536/23.1; 530/350
(58) Field of Search ........................ 536/23.1; 435/69.1, 435/252.3, 325, 320.1

(56) References Cited

PUBLICATIONS

Monsma et al. 1988; Genes & Development 2:2063–1073.*
Coulthart et al., "Differing Amounts of Genetic Polymorphism in Testes and Male Accessory Glands of *Drosophila Melanogaster* and *Drosophila simulans*," *Biochem. Genet,* 26:153–64 (1988) (abstract only).
Stumm–Zollinger et al., "Gene Expression in Male Accessory Glands of Interspoecific Hybrids of *Drosophila*," *J. Insect. Physiol.,* 34(1):59–74 (1988) (abstract only).
Monsma, Dissertation: Structure and Expression of Two *Drosophila melanogaster* Male Accessory Gland Genes, and the Fate of Their Products After Transfer to the Female Fly During Mating, *Diss. Abstr. Int. B.,* 51(4):1656–B (1990) (abstract only).
Aguadéet al., "Polymorphism and Divergence in the *Mst26A* male Accessory Gland Gene Region in Drosophila," *Genetics,* 132:755–770 (1992).
Simmerl et al., "Structure and Regulation of a Gene Cluster for Male Accessory Gland Transcripts in *Drosophila melanogaster*," *Insect Biochem. Mol. Biol.,* 25:127–137 (1995) (abstract only).

Coleman et al., "A *Drosophila* Male Accessory Gland Protein That is a Member of the Serpin Superfamily of Proteinase Inhibitors is Transferred to Females During Mating," *Insect Biochem. Mol. Biol.,* 25(2):203–207 (1995) (abstract only).
Bertram, "Dissertation: Cell Type–Specific Gene Expression in the *Drosophila melanogaster* Male Accessory Gland and the Characterization of an Acdessory Gland Protein," *Diss. Abstr. Int. B.,* 55(7):2509–B (1995) (abstract only).
Clark, "Variation in Sperm Displacement and Its Association with Accessory Gland Protein Loci in *Drosophila melanogaster*," *Genetics,* 139:189–201 (1995).
Herndon et al., "A *Drosophila* Seminal Fluid Protein, Acp26Aa, Stimulates Egg Laying in Females for 1 Day After Mating," *Proc. Natl. Acad. Sci. U.S.A.,* 92:10114–10118 (1995).
Chatterji et al., "A Recombination–Efficient Baculovirus Vector for Simultaneous Expression of Multiple Genes," *Gene,* 171(2):209–213 (1996) (abstract only).
Chen, "The Accessory Gland Proteins in Male *Drosophila*: Structural, Reproductive, and Evolutionary Aspects," *Experientia (Basel)*, 52(6):503–510 (1996) (abstract only).
Hughes, "Quantiative Genetics of Sperm Precedence in *Drosophila melanogaster*," *Genetics,* 145:139–151 (1997).
Wolfner et al., "New Genes for Male Accessory Gland Proteins in *Drosophila melanogaster*," *Insect Biochem. Mol. Biol.,* 27(10):825–834 (1997).
Park et al., "Two Tightly–Linked *Drosophila* Male Accessory Gland Transcripts with the Same Developmental Expression Derive from Independent Transcription Units," *Mechanisms of Development,* 48:51–57 (1994).
Herndon et al., "Mating and Hormonal Triggers Regulate Accessory Gland Gene Expression in Male *Drosophila*," *J. Insect Physiol.,* 43(12):1117–1123 (1997).
Tsaur et al., "Positive Selection and the Molecular Evolution of a Gene of Male Reproduction, Acp26Aa of *Drosophila*," *Mol. Biol. Evol.,* 14(5):544–549 (1997).
Tram et al., "Seminal Fluid Regulation of Female Sexual Attractiveness in *Drosophila melanogaster*," *Proc. Natl. Acad. Sci. USA,* 95:4051–4054 (1998).

* cited by examiner

*Primary Examiner*—Karen Cochrane Carlson
(74) *Attorney, Agent, or Firm*—Nixon Peabody LLP

(57) ABSTRACT

The present invention provides a number of accessory gland proteins from *Drosophila*. The invention also provides an accessory gland protein which is toxic to insect cells and can be used to kill or inhibit the development of insects. Methods of controlling insects are also provided.

23 Claims, 7 Drawing Sheets

| Gene | Genomic Map | mRNA | | | | | Predicted protein | | | | Accession # |
|---|---|---|---|---|---|---|---|---|---|---|---|
| | | Size (kb) | 5'UTR (nt) | ...AUG | 3'UTR (nt) | pA sig. (nt) | ORF (aa) | Signal seq. | Features | | |
| Acp29AB | | 0.95 | 28 | GGAC | 43 | 11 | 234 | 21 | | | U85758 |
| Acp31F | | 3.5,1.5 | ND | ND | ND | ND | ND | ND | | | U85764, U90948 |
| Acp32CD | | 0.95 | * | CUAC | 35 | 17 | 241 | 27 | | | U90950, U85765 |
| Acp33A | | 0.45 | 18, 195 | CAAG, GUAU | 186, 21 | 28 | 47, 43 | 27, 22 | | | |
| Acp36DE | | 2.7 | 198 | AGAU | 126 | 33 | 718 | - | | | U85759 |
| Acp53Ea | | 0.6 | 26 | UCCA | 51 | 11,29 | 120 | 23 | | | U85760 |
| Acp53Eb | | 0.4 | ND | ND | ND | ND | ND | ND | | | |
| Acp62F | | 0.45 | 23 | UACA | 54 | 14 | 115 | 14 | PhTx2-6 similar | | U85763 |
| Acp63F | | 0.45 | 9 | CAAG | 61 | 13,24 | 81 | 16 | | | U85761 |
| Acp76A | | 1.3 | * | GAAA | 44 | 18 | 388 | 14 | serpin signature | | U90947 |
| Acp98AB | | 0.3 | * | UUAA | 62 | 18 | 31 | 14 | | | U85762, U90949 |
| Acp rep1 | | 1.6 | ND | ND | ND | ND | ND | ND | | | |

*FIG. 1*

```
Acp29AB
myasnllyll alwnlwdlsg gQQDIPNGKA TLPSPQTPQN TIDQIGINQN YWFTYNALKQ
NETLAIIDTM EMRIASSLLE FKAQMEIQLQ PLKIIMRHHA SNIKASNNIK MRRFEKVGSR
HFHIEKNLMQ TWFEAYVTCR KMNGHLANIQ DEKELDGILA LAPNNSYWID ISKLVENGGT
FVSTLTGREP FFVKWKSNQD TKKKNQCVYI YAKEMSYDEC PEKKSFVCQA DQWA
                                                        234aa Acp32CD
mnfafnnnnp dgeggtgvdg ggggaggGAA GPGGGTGDSP HSQEGDGSAA TDNPNDDHAT
SADNSLATDG DAIGKKESGG GSDGKSDSKD SSGGNDATPA NGHDDDNDDS DRRMPRIDKI
RKRRPDRRGS APITAITVAT RSDRRQLWRA VRAVHLREQR EPRTFGSNAG SNQRTMEPVR
AVRRTRMPRK WPAKRLLNGQ ATCQMDPKLE PRKMTTRRCN TTGRSDHRFA RGTLEERRHF
N                                                        241aa Acp33A
ORF 1
mlpskrvpfl ftiilflagl gqhttesVLP DCVLYPRCLI TKDPCCM       47aa ORF 2
mevemwfkis allkavtkta lcFYKYKYPQ ISGLNMATFQ VFQ           43aa Acp36DE
MQILSRNPRR SHNLPHNLNQ MHLHNSRHRS KAIDCWENPP VSESQSQSES QSQSESQKQS
QSQSQRQQQI QTQLQILRQL QQKSNEQSAA QSASQIQSQR QSDSQSNLQL QEQSQSQSEQ
GKPIQSQIQI LQGLQQKELD DKSASQSQSE SKTRKEQQKQ LNLQQLEELS SSLSQSRLGL
GQQIQSQLQK NQLDKQFSSQ FQSQSKSQLE QQMQLQLQSL RQLQQKQLDE QSASQSQPQS
QVAQQIQSHL QLLRLLQSRL KTQSALKSDL EQQILPQLKK LTEVQQKQLA EQPTLRPSSK
SQSPGQLEQQ ILLHLQNLLH FQQNQLKSDT QTQSQLQESK SNSLSQSQSQ SQEQLQLQRD
QNLRQLEQVK LEMQNIRELL QKGKSELQTQ SDSQRRIHEL YQNILQLNKE KLSYQLKQLK
LKELEDQKKS QAEISKGSNP SNLFIIGQLP SEGKPAPGNQ GPSIEPKLVP QPGSLDKLPS
GGGLIGKPAS TGLYILSPDF NDLSDYRDQP RLQQELKKHQ NILSLLQRRQ NDKKQQNAQL
LLGQQQKEQQ AQESINKQQS SSAGSSSQTK LQQDIQSTGA QGSQQGLQAG STGLQTSSLQ
GTESSASQSA LQRLKEQEQL RIQTENDQKT SSSSSHSNSQ NSQSSSSQSS QASQSEAQRQ
EAGNRNTLLL DQSSSKTQSS RSPSRRLNHR HIHRRSQRRT HLQTFNRNYK EKAKRC
                                                        716aa Acp53Ea
mklikvtlvf sllalvfvaq teaQNPIWEN WLACNRIGTK ALASLLRETI PTVRNLLNCI
DFNPPTDIGN SYLSKLKLYY ELVKRGALDK TQCLIVPLKE SVRLLRPYVK SLETNKCLGE
                                                        120aa Acp62F
mtdmwslkic aclgLLLLFK PIDSMGWQGP KVDCTANGTQ TECPVACPET CEYSGNGPCV
KMCGAPCVCK PGYVINERIP ACVLRSDCPK DVVRKEDMLL GVSNFKCFSR NYNCS
                                                        115aa Acp63F
mkaiivfilf issvhaMSKC NQAIYLNLDP HCGILPDCNL DGPNPSYLNR VSCERKENGK
PGFIELIPGK CLHGKPRCSL K                                  81aa Acp76A
mgnhqvtflv lctsLLFQNT IQQNVSFQLI REIDRYTPEN FVLSVLNIEM ILFEIHAAKA
VESNNDLERS LIINFGYSEA RQEVLDWGLR YKKASSAKFQ MANKVAVSQK LPLSQKLRLV
NEVLMTSAKK YDVTKDVRPS KLMDEWLSSH LDGVLANFVQ EKKLNAGENI VAISGMTVTP
LWASHFQSEI NRYFVNNPGT GYASKDPTCV PMMHSLSSFE TMSTDEAKGI YIPFSSANLG
MLILLPRKGV TCKDILDNLN NQINVEYNDH KDVHLLLPIF KEKFDYNIAK FFNGINIEDT
FKDSAFKSKA KIKINNPRVN HGIRFQPILR LEVVDDINTG KTETFEVNRP FVFVIKDKVN
VYAVGRIENL DGLTDKVNCS KKYADLKS                           388aa Acp98AB
mefpnpvlsr igrsLRTNKG THYQRMTRMS K                       31aa
```

GENES FOR MALE ACCESSORY GLAND PROTEINS IN DROSOPHILA MELANOGASTER

The present application is a divisional of U.S. patent application Ser. No. 09/219,983, filed Dec. 23, 1998, now U.S. Pat. No. 6,380,159, which claims the benefit of U.S. Provisional Patent Application Ser. No. 60/071,315, filed Dec. 23, 1997.

The subject matter of this application was made with support from the United States Government under Grant Nos. IBN97-23356, IBN94-06171, and DCB91-08221 from the National Science Foundation. The United States Government may retain certain rights.

BACKGROUND OF THE INVENTION

After mating, behavioral and physiological changes are seen in the female insect. Compared to virgins, mated *Drosophila melanogaster* females are largely unreceptive to further mating, lay eggs at an elevated rate, live less long, and store and efficiently utilize sperm (reviewed in Hall, 1994; Chen, 1996; Kubli, 1996; Wolfner, 1997). These changes in the female occur because she receives, via seminal fluid, secretions from her mate's accessory gland and also sperm (see Chen, 1996; Kubli, 1996; Wolfner, 1997 for reviews and for original references). Products of the predominant cell type of the accessory gland, the main cells, are necessary for changes in the female's egg-laying rate and receptivity on the first day after mating. Stored sperm cause these effects to persist for up to 11 days following mating. Accessory gland main cell secretions also shorten the life span of the mated female. In addition, they play a role in the storage of sperm and in the competition between sperm from sequential matings.

Knowledge of how accessory gland products mediate these changes is important in understanding the control of insect fertility and the mechanisms of peptide hormone action. Once genes encoding Accessory gland proteins (Acps) are identified, genetic and molecular genetic techniques uniquely possible in *Drosophila* can be used to dissect the role of each protein in reproduction. In a few cases, it is possible to identify the functions of Acps by injecting purified fractions into unmated female flies and observing behavioral effects. For example, in *D. melanogaster*, a "sex peptide" ("SP") of 36 amino acids was purified and shown to stimulate egg-laying and depress receptivity to mating for one day (Chen, 1988). SP was cloned and shown to derive from a single gene at chromosomal position 70A (Chen, 1988). A sex peptide and a second peptide, ovulation-stimulating substance (OSS), with similar activities have also been purified from *D. suzukii* (Ohashi, 1991, Schmidt, 1993).

Only Acps which can be purified or synthesized in active forms, act on their own and act via the hemolymph, can be identified by such assays. In order to identify Acp genes without presupposition of function, differential cDNA hybridization can be used to isolate RNAs expressed only in accessory glands (Schäfer, 1986; DiBenedetto, 1987; Monsma and Wolfner, 1988). cDNA hybridization screens are more likely to isolate abundant RNAs in a tissue. Thus, they are biased towards RNAs expressed in main cells of the accessory gland (96% of the secretory cells of the accessory gland; Bertram, 1992) rather than the rarer secondary cells (4% of the secretory cells of the gland; Bertram, 1992). Previous differential cDNA hybridization screens for genomic clones encoding male-specific transcripts identified three genomic regions encoding Acps (Schäfer, 1986; DiBenedetto, 1987). Of these, the 95EF region encodes a small secreted Acp (DiBenedetto, 1990), 57D contains a gene cluster encoding three small peptides (Simmerl, 1995), and the 51F locus has not yet been characterized. In addition to these genes, a region encoding two Acps has been identified by screening a "chromosomal walk" for accessory gland-specific transcription units (Monsma and Wolfner, 1988). In this region, only 20 bases separate the gene for Acp26Aa, an ELH-similar prohormone-like molecule (Monsma and Wolfner, 1988) that stimulates egg-laying in the mated female fly (Herndon and Wolfner, 1995), from the gene for Acp26Ab, a small peptide of as yet unknown function (Monsma and Wolfner, 1988). The previously-isolated Acp genes are only a small subset of Acp genes, though the total number of Acp genes is difficult to estimate from prior protein electrophoretic data (e.g. Ingman-Baker and Candido, 1980; Stumm-Zollinger and Chen, 1985; Whalen and Wilson, 1986; Coulthart and Singh, 1988) as summarized and discussed in Chen (1991). This is because on the one hand in the electrophoretic studies small peptides were not resolved, while on the other hand some Acps run as multiple bands on SDS gels (Monsma and Wolfner, 1988). To gain a more complete picture of the spectrum of proteins produced by the accessory gland, a differential screen aimed directly at accessory gland-specific RNAs was performed.

SUMMARY OF THE INVENTION

The present invention provides an isolated nucleic acid molecule encoding an accessory gland protein from *Drosophila* which has the biological property of an insect toxin.

The invention further provides an isolated nucleic acid molecule encoding an amino acid sequence sufficiently duplicative of the accessory gland protein encoded by the nucleic acid molecule of SEQ. ID. No. 2 so that a polypeptide expressed from the nucleic acid molecule has the biological property of an insect toxin.

Another embodiment of the invention is an isolated *Drosophila melanogaster* insect toxin protein.

The invention also provides a method of reducing an insect's life span. The insect is contacted with an isolated *Drosophila* insect toxin protein under conditions effective shorten the insect's life span.

Yet another embodiment of the invention is a method of reducing an insect's life span by contacting the insect with an expression vector containing a nucleic acid molecule encoding a *Drosophila* insect toxin protein under conditions effective to express the protein.

The invention also provides isolated nucleic acid molecules having the nucleotide sequences of SEQ. ID. No. 2, SEQ. ID. No. 5, SEQ. ID. No. 8, SEQ. ID. No. 13, SEQ. ID. No. 18, SEQ. ID. No. 21, SEQ. ID. No. 24, SEQ. ID. No. 27, or SEQ. ID. No. 30, or a nucleic acid molecules which hybridizes under stringent conditions to a nucleic acid molecule having a nucleic acid sequence of SEQ. ID. No. 2, SEQ. ID. No. 5, SEQ. ID. No. 8, SEQ. ID. No. 13, SEQ. ID. No. 18, SEQ. ID. No. 21, SEQ. ID. No. 24, SEQ. ID. No. 27, or SEQ. ID. No. 30.

The present invention also provides isolated proteins having an amino acid sequence of SEQ. ID. No. 4, SEQ. ID. No. 7, SEQ. ID. No. 11, SEQ. ID. No. 12, SEQ. ID. No. 16, SEQ. ID. No. 17, SEQ. ID. No. 20, SEQ. ID. No. 23, SEQ. ID. No. 26, SEQ. ID. No. 29, or SEQ. ID. No. 32.

Yet another embodiment of the invention is a method for determining whether a female *Drosophila melanogaster* has recently mated. An antibody, fragment thereof, or probe which recognizes a protein having a sequence provided in SEQ. ID. No. 4, SEQ. ID. No. 7, SEQ. ID. No. 11, SEQ. ID. No. 12, SEQ. ID. No. 16, SEQ. ID. No. 17, SEQ. ID. No. 20, SEQ. ID. No. 23, SEQ. ID. No. 26, SEQ. ID. No. 29, or SEQ. ID. No. 32 is provided. The antibody, fragment thereof, or probe is bound to a label effective to permit detection of the protein upon binding of the antibody, fragment thereof, or probe to the protein. The labeled antibody is contacted with a fluid or tissue sample from *Drosophila melanogaster* under conditions effective to permit binding of the antibody, fragment thereof, or probe to the protein. The presence of any of the protein in the biological sample is detected by detecting the label.

BRIEF DESCRIPTION OF THE DRAWINGS

FIG. 1 depicts the genomic organization and transcript characteristics of new Acp genes. Gene name, position and copy number: The genes are named Acp followed by their location on the polytene chromosomes as determined by in situ hybridization. The site for Acp76A is determined as 75F/76A, for 63F is 63F/64A, for 31F is 31F/32A. The genomic clone containing Acp33A has aminor site of hybridization at 32E.

Restriction map: The map of the genomic region containing the accessory gland transcript is shown, to a scale such that the leftmost EcoRI-XbaI fragment of Acp31F is 1.0 kb. In all cases but 2, the map is derived from a single genomic clone of the region. The larger region covered for Acps 36DE and 33A is a composite of the overlapping maps of three genomic clones each. The genomic fragment(s) that hybridize to the Acp transcript is shown as a thicker line. The clones are oriented with the Acp gene transcription direction from left to right, except for Acps 31F, 53Eb and rep1, where the transcription direction was not determined. E=Eco RI, H=Hin dIII, B=Bam HI, X=Xba I, S=Sal I, Bgl=Bgl II, N=Ngo M1, P=Pml I, W=Swa I.

Transcript characteristics: The size of each poly A+ accessory gland transcript was determined on a minimum of three independent Northern blots. The number of bases (nt) in the cDNA clone before the first AUG is listed (5' UTR); since the cDNA clones may not be full-length, the size of this untranslated leader should be taken as a minimum. For all genes except Acp36DE, the longest open reading frame begins with the first AUG. As noted in the text, although Acp36DE has a short open reading frame beginning at base 18 of the cDNA sequence (and preceded by AUUA), the Acp is encoded by the longer second open reading frame which is the one listed in the figure.

The four bases immediately 5' of the initiating AUG are shown; those matching consensus (C/A A A C/A; Cavener, 1987) are underlined. The column headed 3'UTR gives the number of bases from the translational stop codon to the beginning of the poly A tail. For Acp53Ea, the cDNA clone did not contain the polyA tail. Thus the size of its UTR is a minimum The distance of that tail from the AAUAAA signal (or its best, 5/6, match) is given in the "pA sig." column.

The GenBank accession numbers for these sequences are given. For Acps 32CD and 98AB, the sequences reported are composites of overlapping genomic and cDNA sequences. GenBank requires that genomic and cDNA sequences be given separate accession numbers. For each of these genes, the first number listed is for the genomic sequence, the second for its partially-overlapping cDNA. For Acp76A, the accession number is for genomic sequence, which completely contains the cDNA sequence of this apparently intron-less mRNA. The other accession numbers are for cDNA sequences. Two accession numbers are given for Acp33A, since GenBank requires that each predicted ORF in this single mRNA be listed with its own accession number. The nucleotide sequences for these two accession numbers are, of course, the same.

Characteristics of predicted Acp: The number of amino acids (aa) in the Acp-encoding ORF, the length of the hydrophobic sequence terminating at a predicted signal sequence cleavage site (von Heijne, 1983) and predicted features of the Acp are listed in successive columns.

Figure 2A:
Figure 2B:
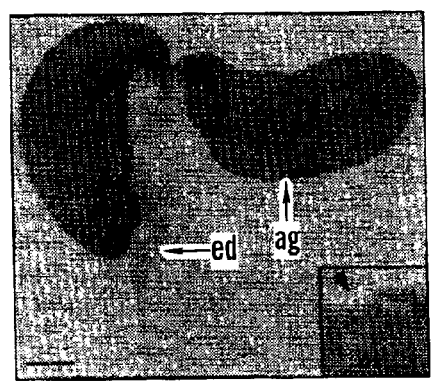

FIGS. 2A and 2B show the expression of an accessory gland gene, Acp36DE, as an example. FIG. 2A is a representative Northern blot of male accessory gland RNA and female RNA probed with radiolabeled RNA complementary to Acp36DE. A male specific RNA of 2.6–2.7 kb is detected. The blot was probed separately with sequences complementary to actin as a loading control as in DiBenedetto (1987), which confirmed that equivalent amounts of RNA were present in the two lanes. FIG. 2B provides a representative in situ hybridization to whole-mount accessory glands from a 3-day-old virgin male. The probe was the digoxigenin-labeled 2.1 kb EcoRI fragment of Acp36DE cDNA clone #11A (Bertram, 1994). Staining is seen in the accessory glands ("ag"), but not in the ejaculatory duct ("ed"). Bar= 0.128 millimeter. FIG. 2B (inset) is a higher magnification of the distal tip of an accessory gland from a similar in situ hybridization. Main cells are stained. Secondary cells are not stained. This can be seen most clearly at the edge of the gland, where an arrowhead points to an unstained secondary cell (the apparent "bite" taken out of the edge of the stained tissue is the unstained cell). Other secondary cells, lying atop a layer of stained main cells and themselves surrounded by stained main cells, are seen as light circles. Bar=0.051 millimeter.

FIG. 3 provides the predicted protein sequences of new Acps. The predicted protein sequence from the single long ORF in each Acp's cDNA is shown. For Acp33A, both ORFs are shown; ORF1 is the more 5' one. The potential signal sequence is written in lower case. Potential N-linked glycosylation sites (N-x-S/T/C; Kornfeld and Kornfeld, 1985; Miletich and Broze, 1990), amidation site (IGKK; Kreil, 1984; Bradbury and Smyth, 1987), glycosaminoglycan attachment sites (SGxG; Hassell, 1986; Bourdon, 1987) and basic amino acids (K, R) in contexts consistent with prohormone processing cleavages (Schwartz, 1986; Benoit, 1987; Nakayama, 1992) are underlined. The amino acids that match serpin consensus in Acp76A, and those in Acp62F that are similar to toxin PhTx2-6 are boxed. Sequencing of genomic DNA upstream from the 5' end of the incomplete cDNA of Acp32CD led to the discovery of an ORF encoding 329 amino acids. This ORF is too long to be encoded on the 0.95 kb Acp32CD RNA, whose size includes a poly A tail. Therefore, it is surmised that Acp32CD corresponds to the 241 amino acid sequence shown in the figure, which begins at the second AUG of the 329-amino acid ORF (AGAU immediately precedes the AUG of the long ORF). The amino acids encoded by genomic sequence immediately upstream of the sequence shown in this figure are: mppllrhcfg hafiglplfn GQEQPRPQSN RFDSGQRRSS LYIRDGRTAR AAQRCSDVAD ADAATHWLLG PVAL-GQLPEH GALGQKYY (SEQ. ID. No. 1).

FIG. 4 is a best-fit alignment of similar regions of Acp62F (aa residues 46–73 of SEQ. ID. No. 4) and PhTx2-6 (SEQ. ID. No. 35, an residues 9–35 of the full length PhTx2-6 protein).

Figure 5:
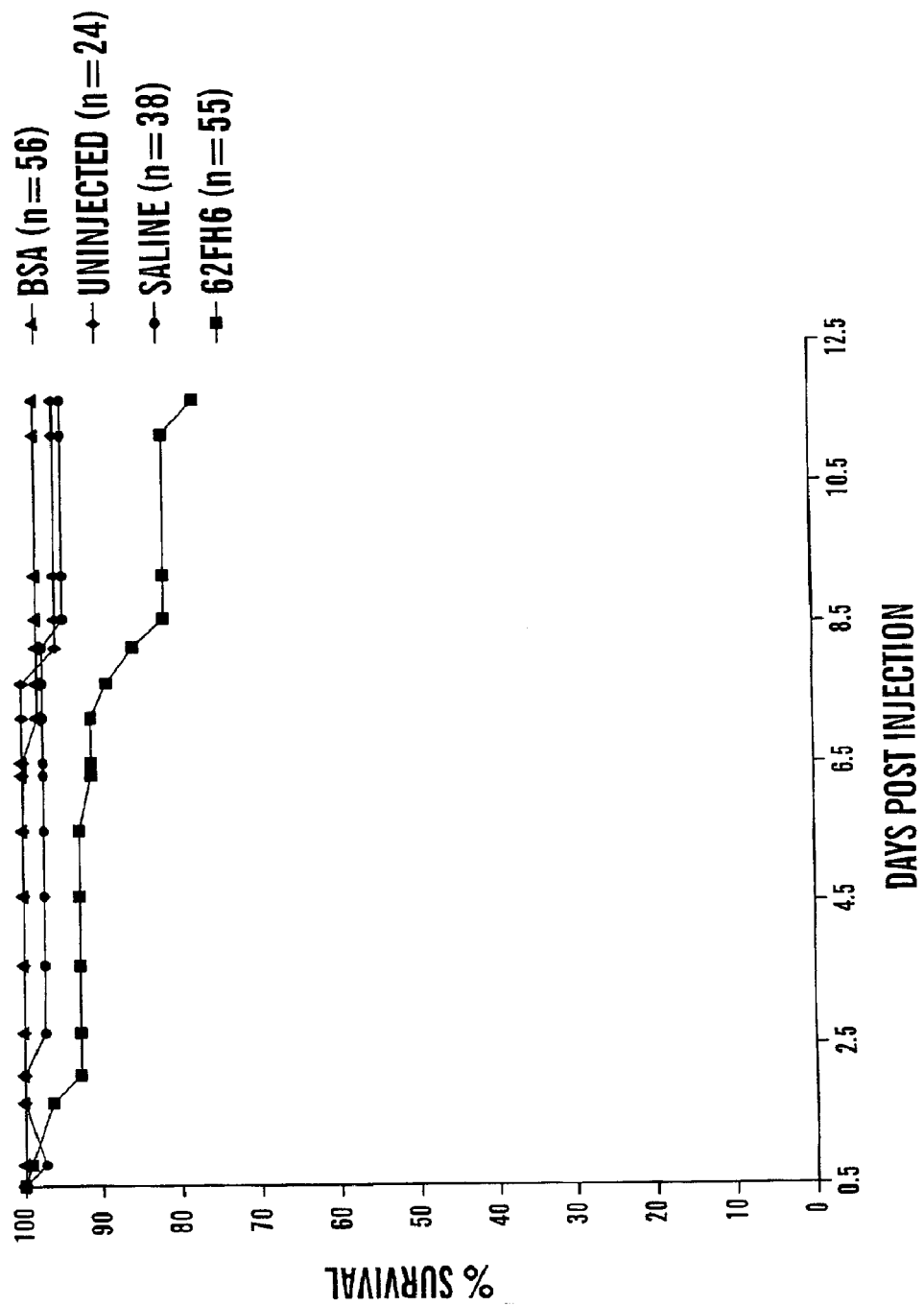

FIG. 5 shows the rate of survival of baculovirus injected 5th instar *Trichoplusia ni*. The results of controls and baculovirus which express Acp62F are included.

Figure 6:
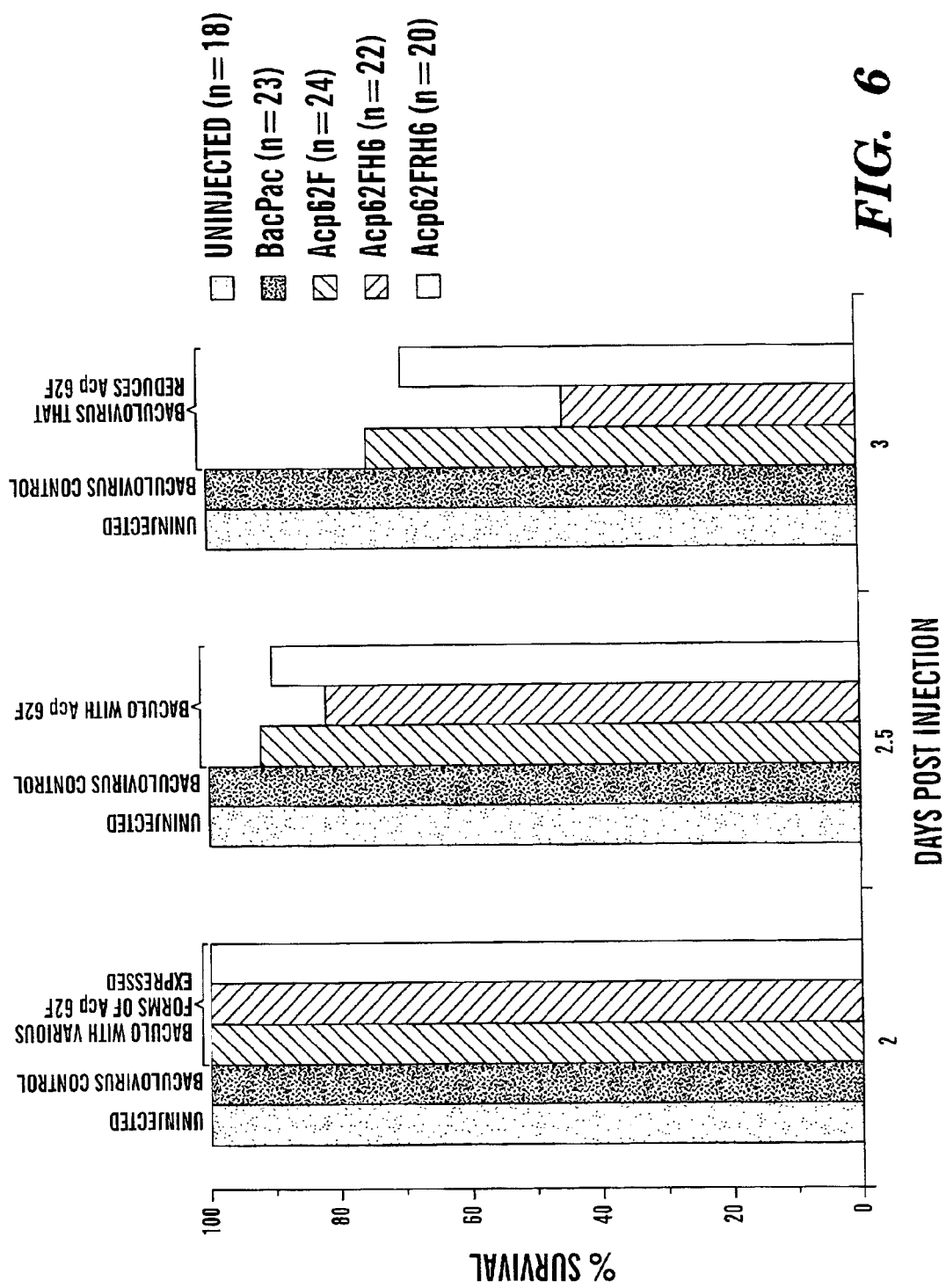

FIG. 6 shows the rate of pupation of 3$^{rd}$ instar *Trichoplusia ni* after injection with Acp62F protein.

Figure 7:
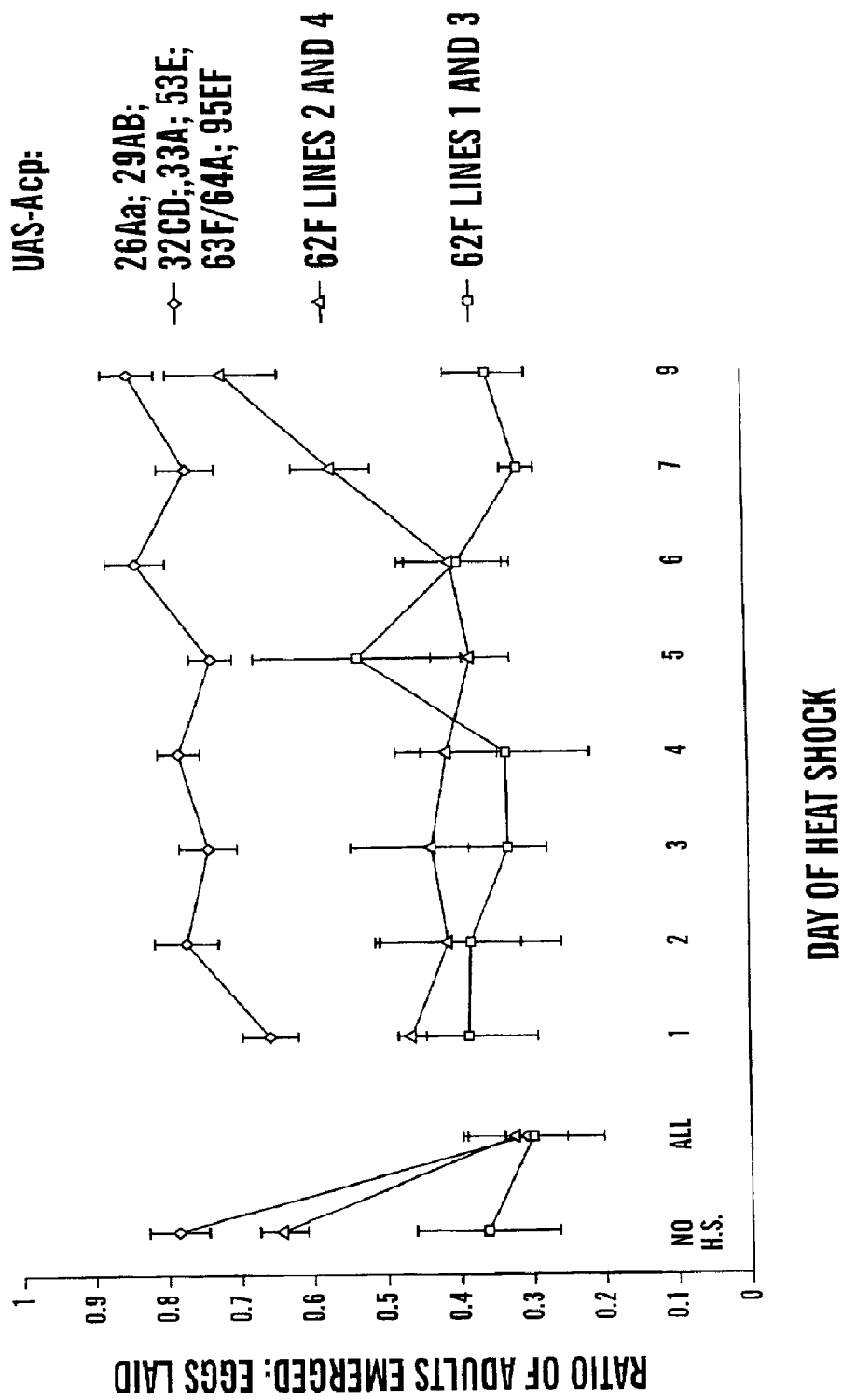

FIG. 7 shows the effect on survival of Acp62F expression in pre-adult fruit flies.

DETAILED DESCRIPTION OF THE INVENTION

The present invention provides isolated genes encoding 12 previously unreported accessory gland-specific mRNAs from the fruit fly *Drosophila melanogaster*. The restriction maps of the new genes, the chromosome positions—which are all autosomal—of the 11 non-repetitive genes, their expression patterns, and the sequences of the Accessory gland proteins (Acps) encoded by 9 of the genes are provided.

The present invention provides an isolated nucleic acid molecule encoding an accessory gland protein from *Drosophila* which has the biological property of an insect toxin. The 115 amino acid Acp62F has a 28 amino acid region of high sequence similarity to a neurotoxin of the Brazilian armed spider *Phoneutria nigriventer*. In a preferred embodiment of the invention, the accessory gland protein has greater than 40% sequence similarity to amino acids 9 to 35 of the PhTx2-6 toxin of *Phoneutria nigriventer*. This protein has been tested and has been shown to kill or inhibit the growth of insects. In particular, the accessory gland protein is toxic to *Drosophila* or *trichoplusia*.

The present invention provides a gene encoding Acp62F. The cDNA sequence of the Acp62F gene is as follows (SEQ. ID. No. 2):

be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology" is conserved).

Alternatively, suitable DNA sequences may be identified by hybridization to the disclosed sequences which encode the accessory gland proteins under stringent conditions. For example, sequences can be isolated that hybridize to a DNA molecule comprising a nucleotide sequence of approximately 50 continuous bases of the sequences encoding the accessory gland proteins under stringent conditions characterized by a hybridization buffer comprising 0.9M sodium citrate ("SSC") buffer at a temperature of 37° C. and remaining bound when subject to washing with the SSC buffer at 37° C.; and preferably in a hybridization buffer comprising 20% formamide in 0.9M saline/0.09M SSC buffer at a temperature of 42° C. and remaining bound when subject to washing at 42° C. with 0.2×SSC buffer at 42° C.

Another embodiment of the invention is an expression vector carrrying the nucleic acid molecule encoding Acp62F.

The DNA molecule encoding the accessory gland proteins can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements

```
  1 ggtagacgta ttccccatct acaatgacgg acatgtggag cttgaagatc tgtgcctgtc 61 tgggccttct attacttttc aaacccatcg actccatggg atggcaagga cctaaagttg 121 actgtacggc caacggaact cagacggagt gtcctgtagc atgtcctgaa acctgcgagt 181 actccggcaa tggaccctgc gtcaagatgt gcggagctcc ttgtgtgtgt aagccgggat 241 atgttatcaa tgagaggatt ccggcctgtg ttctgcgatc cgattgccca aaagatgttg 301 ttcgaaagga agatatgcta ctgggtgtat cgaactttaa gtgctttagc agaaattaca 361 actgttcata gaaatttatt aggaaggcag ctaaacttta aactaaaata caataaaatg 421 taaataaaaa aaaaaaaaa
```

In a preferred embodiment of the invention, the isolated nucleic acid moleucle has a nucleotide sequence according to SEQ. ID. No. 2, or a nucleic acid molecule which hybridizes under stringent conditions to a nucleic acid molecule having the nucleic acid sequence of SEQ. ID. No. 2.

The nucleic acid molecule can be deoxyribonucleic acid (DNA) or ribonucleic acid (RNA), genomic or recombinant, biologically isolated or synthetic. The invention encompasses the DNA sequences as well as their complements. The DNA molecule can be a cDNA molecule, which is a DNA copy of a messenger RNA (mRNA) encoding the accessory gland protein. A suitable RNA molecule is mRNA.

Suitable nucleic acid molecules include those nucleic acid molecules encoding an accessory gland protein and having a nucleotide sequence which is at least 95% homologous to the nucleotide sequence of an accessory gland protein of the present invention.

While the nucleotide sequence is at least 95% homologous, nucleotide identity is not required. As should for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/− or KS+/− (see Stratagene, 1993), pQE, pIH821, pGEX, pET series (see Studier, 1990), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook, (1989).

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

In a preferred embodiment, the expression vector is a viral vector. In a more preferred embodiment, the viral vector is a baculovirus vector. Baculovirus vectors, which are derived from the genome of the AcNPV virus, are designed to provide high level expression of cDNA in the Sf9 line of insect cells. A baculovirus vector is constructed in accordance with techniques that are known in the art, for example, as described in Kitts, (1993); Smith, (1983); and Luckow and Summer, (1989). In one embodiment of the present invention, a baculovirus expression vector is constructed substantially in accordance to Summers and Smith, (1987). Moreover, materials and methods for baculovirus/insect cell expression systems are commercially available in kit form, for example, the MaxBac Registered TM kit from Invitrogen (San Diego, Calif.). Recombinant baculoviruses are generated by homologous recombination following co-transfection of the baculovirus transfer vector and linearized AcNPV genomic DNA (Kitts, 1990) into Sf9 cells.

In yet another embodiment, the invention provides a host cell having the expression vector carrying the accessory gland protein gene. In a preferred embodiment, the host cell is an insect cell.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, (1979).

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in E. coli, its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in E. coli requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the E. coli tryptophan E, D, C, B or A genes. Additionally, any SD-ATG combination produced by recombinant DNA or other techniques involving incorporation of synthetic nucleotides may be used.

Once the isolated DNA molecule encoding the accessory gland protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The invention also provides an antisense nucleic acid molecule that is complementary to the mRNA encoding the the accessory gland protein, or a fragment thereof capable of hybridizing under stringent conditions to the mRNA. The antisense nucleic acid molecule is ribonucleic acid. This antisense molecule can base-pair with the mRNA, preventing translation of the mRNA into protein.

The invention further provides an isolated fragment of the nucleic acid molecule encoding the accessory gland protein. Nucleic acid molecules encoding the accessory gland proteins, and fragments of the nucleic acid molecules, are thus provided.

Each of the nucleic acid molecules, fragments thereof, antisense nucleic acid molecules, and fragments thereof, can be expressed in suitable host cells using conventional techniques. Such techniques may involve the use of expression vectors which comprise the nucleic acid molecules, fragments thereof, antisense nucleic acid molecules, or fragments thereof. These expression vectors can then be used to transform suitable host cells.

Host cells transformed with nucleic acid molecules encoding the accessory gland protein can be used to produce accessory gland proteins (or cells transformed with the fragments can be used to produce fragments of the accessory gland proteins). Alternatively, the fragments or full-length accessory gland proteins can be produced synthetically using the sequence information of the accessory gland proteins and fragments. In host cells transformed with the antisense nucleic acid molecules, or fragments thereof, the antisense nucleic acid molecules or fragments thereof will block translation of the accessory gland protein. Accordingly, in host cells transformed with the antisense nucleic acid molecules or fragments thereof, the expression of accessory gland protein is decreased.

The invention also provides an isolated nucleic acid molecule having a nucleic acid sequence encoding an amino acid sequence sufficiently duplicative of the accessory gland protein encoded by the disclosed nucleic acid molecules so that a polypeptide expressed from the nucleic acid molecule has the biological property of an insect toxin. The cDNA for Acp62F includes an open reading frame beginning at position 24 of the cDNA sequence. The open reading frame sequence is provided in SEQ. ID. No. 3.

techniques. In accordance with the present invention, the accessory gland proteins are isolated from host cells. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example Ausubel (1994). Additionally, antibodies can be prepared against substantially pure preparations of the protein. See, for example, Radka, (1983) and Radka, (1984). Any combination of methods may be utilized to purify protein having pesticidal properties. As the protocol is being formulated, pesticidal activity is determined after each purification step, if relevant.

Fragments of the above polypeptide or protein are also encompassed by the present invention. Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide that can be tested for an accessory gland protein.

```
  1 atgacggaca tgtggagctt gaagatctgt gcctgtctgg gccttctatt acttttcaaa
 61 cccatcgact ccatgggatg gcaaggacct aaagttgact gtacggccaa cggaactcag
121 acggagtgtc ctgtagcatg tcctgaaacc tgcgagtact ccggcaatgg accctgcgtc
181 aagatgtgcg gagctccttg tgtgtgtaag ccgggatatg ttatcaatga gaggattccg
241 gcctgtgttc tgcgatccga ttgcccaaaa gatgttgttc gaaaggaaga tatgctactg
301 ggtgtatcga actttaagtg ctttagcaga aattacaact gttca
```

The present invention also provides an isolated *Drosophila melanogaster* insect toxin protein. The amino acid sequence of the Acp62F protein is provided in SEQ. ID. No. 4, as follows:

```
 1 MTDMWSLKIC ACLGLLLLFK PIDSMGWQGP KVDCTANGTQ TECPVACPET CEYSGNGPCV

61 KMCGAPCVCK PGYVINERIP ACVLRSDCPK DVVRKEDMLL GVSNFKCFSR NYNCS
```

As an alternative, fragments of an accessory gland protein can be produced by digestion of an accessory gland protein with proteolytic enzymes like chymotrypsin or *Staphylococcus* proteinase A, or trypsin. Different proteolytic enzymes are likely to cleave accessory gland proteins at different sites based on the amino acid sequence of an accessory gland protein.

In another approach, based on knowledge of the primary structure of the protein, fragments of the accessory gland protein gene may be synthesized by using the PCR technique together with specific sets of primers chosen to represent particular portions of the protein. These then would be cloned into an appropriate vector for increased expression of an accessory peptide or protein.

Chemical synthesis can also be used to make suitable fragments. Such a synthesis is carried out using known amino acid sequences for the accessory gland protein being produced. Alternatively, subjecting a full length accessory gland protein to high temperatures and pressures will pro- In a preferred embodiment, the isolated *Drosophila melanogaster* insect toxin protein has greater than 40% sequence similarity to amino acids 9 to 35 of the PhTx2-6 toxin of *Phoneutria nigriventer*. Another preferred embodiment is where the isolated *Drosophila melanogaster* insect toxin protein is toxic to *Drosophila* or caterpillar.

The isolated *Drosophila melanogaster* insect toxin protein may have an amino acid sequence according to SEQ. ID. No. 4, or be a protein encoded by a nucleic acid molecule which hybridizes under stringent conditions to a nucleic acid molecule having the nucleic acid sequence of SEQ. ID. No. 2 and which has the biological property of an insect toxin.

The protein or polypeptide of the present invention is preferably produced in purified form (preferably at least about 80%, more preferably 90%, pure) by conventional duce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Gene amplification can also be used to obtain very high levels of expression of transfected gene. When cell cultures are treated with methotrexate ("Mtx"), an inhibitor of a critical metabolic enzyme, dihydrofolate reductase ("DHFR"), most cells die, but eventually some Mtx-resistant cells grow up. A gene to be expressed in cells is cotransfected with a cloned DHFR gene, and the transfected cells are subjected to selection with a low concentration of Mtx. Resistant cells that have taken up the DHFR gene (and, in most cases, the cotransfected gene) multiply. Increasing the concentration of Mtx in the growth medium in small steps generates populations of cells that have progressively amplified the DHFR gene, together with linked DNA. Although this process takes several months, the resulting cell cultures capable of growing in the highest Mtx concentrations will have stably amplified the DNA encompassing the DHFR gene a hundredfold or more, leading to significant elevation of the expression of the cotransfected gene.

Once the nucleic acid molecule encoding an accessory gland protein has been inserted into a host cell, with or without the use of an intermediate expression vector, the host cell can be used to produce the accessory gland protein by culturing the cell under conditions suitable for translation of the DNA molecule, thereby expressing the accessory gland protein. The accessory gland protein can then be recovered from the cell. Generally, the accessory gland protein of the present invention is produced in purified form by conventional techniques, such as by secretion into the growth medium of recombinant E. coli. To isolate the protein, the E. coli host cell carrying a recombinant plasmid is propagated, homogenized, and the homogenate is centrifuged to remove bacterial debris. The supernatant is then subjected to sequential ammonium sulfate precipitation. The fraction containing the protein of the present invention is subjected to gel filtration in an appropriately sized dextran or polyacrylamide column to separate the proteins. If necessary, the protein fraction may be further purified by HPLC.

The present invention also provides an isolated antibody, fragment thereof, or probe which recognizes an accessory gland protein provided by the invention. Preferred antibodies, fragments thereof, or probes are those which recognize a protein having an amino acid sequence according to SEQ. ID. No. 4, or a protein encoded by a nucleic acid molecule which hybridizes under stringent conditions to a nucleic acid molecule having the nucleic acid sequence of SEQ. ID. No. 2 and where the protein has the biological function of an insect toxin.

Antibodies can also be raised to each of the accessory gland proteins, and to the isolated fragments thereof. Antibodies of the subject invention include polyclonal antibodies and monoclonal antibodies which are specific for an accessory gland protein or isolated fragments thereof. In addition to utilizing whole antibodies, the present invention encompasses use of binding portions of such antibodies. Such binding portions include Fab fragments, F(ab')2 fragments, and Fv fragments. Such antibody fragments can be made by conventional procedures, such as proteolytic fragmentation procedures, as described in Goding, (1983). These antibodies or fragments thereof can thus be used to detect the presence of an accessory gland protein in a sample (or to detect the presence of a fragment of an accessory gland protein), by contacting the sample with the antibody or fragment thereof. The antibody or fragment thereof binds to an accessory gland protein or fragment thereof present in the sample, forming a complex therewith. The complex can then be detected, thereby detecting the presence of the accessory gland protein or fragment thereof in the sample.

In a preferred embodiment the antibody, fragment thereof, or probe is a monoclonal antibody. Alternatively, the antibody, fragment thereof, or probe is a polyclonal antibody.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, (1975).

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, (1976). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 ml per site at six different sites. Each injected material will contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed in Harlow, (1988).

In addition to utilizing whole antibodies, the processes of the present invention encompass use of binding portions of such antibodies. Such binding portions include Fab fragments, F(ab')2 fragments, and Fv fragments. These antibody fragments can be made by conventional procedures, such as proteolytic fragmentation procedures, as described in Goding, (1983).

The present invention also provides a method of reducing an insect's life span. The insect is contacted with an isolated Drosophila insect toxin protein under conditions effective shorten the insect's life span. In a preferred embodiment, the isolated Drosophila insect toxin protein used to shorten the life span of the insect has an amino acid sequence corresponding to SEQ. ID. No. 4.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In an alternative embodiment of the invention, the gene encoding the insect toxin protein may be introduced into plants. The gene is under the control of a promoter which is effective in plants, so that the insect toxin gene is expressed in the plant. The insects would ingest the protein when eating any portion of the plant. When utilizing transgenic plants, this involves providing a transgenic plant transformed with a DNA molecule encoding a fragment of a insect toxin protein, which fragment is toxic to the target insect, and growing the plant under conditions effective to permit that DNA molecule to control insects. Alternatively, a transgenic plant seed transformed with a DNA molecule encoding a fragment of a hypersensitive response elicitor polypeptide or protein which fragment is toxic to the target insects can be provided and planted in soil. A plant is then propagated from the planted seed under conditions effective to permit that DNA molecule to control insects.

In addition to contacting the insect with the protein of the invention, the invention provides a method of reducing an insect's life span by contacting the insect with an expression vector containing a nucleic acid molecule encoding a Drosophila insect toxin protein under conditions effective to express the protein. In a preferred embodiment, the Drosophila insect toxin protein is a protein having an amino acid sequence according to SEQ. ID. No. 4, or a protein encoded by a nucleic acid molecule which hybridizes under stringent conditions to a nucleic acid molecule having the nucleic acid sequence of SEQ. ID. No. 2 and where the protein has the biological function of an insect toxin.

The present invention also provides several other accessory gland proteins and the genes encoding the proteins. As discussed above, the genes are named Acp followed by their location on the polytene chromosomes as determined by in situ hybridization. For example, the site for Acp76A is determined as 75F/76A, for 63F is 63F/64A, for 31F is 31F/32A. The genomic clone containing Acp33A has aminor site of hybridization at 32E. Eight of the proteins predicted from these sequences begin with putative secretion signals. Following their signal sequences, three of the predicted molecules are peptides and the other five are larger polypeptides with characteristics of cleavable prohormones. The ninth molecule, which has an N-terminal hydrophobic region but no consensus signal cleavage site, is predicted to be a 716 amino acid glycoprotein. Of the 9 proteins, two have intriguing similarities to sequences in protein databases. Acp76A is a 388 amino acid pro-protein which contains a signature sequence for the serpin class of protease inhibitors.

The invention provides the isolated nucleic acid molecules which encode a number of novel accessory gland proteins. The preferred embodiments of the invention are nucleic acid molecules having a nucleotide sequence of SEQ. ID. No. 2, SEQ. ID. No. 5, SEQ. ID. No. 8, SEQ. ID. No. 13, SEQ. ID. No. 18, SEQ. ID. No. 21, SEQ. ID. No. 24, SEQ. ID. No. 27, or SEQ. ID. No. 30. The present invention also includes nucleic acid molecules which hybridizes under stringent conditions to a nucleic acid molecule having a nucleic acid sequence selected from the group consisting of SEQ. ID. No. 2, SEQ. ID. No. 5, SEQ. ID. No. 8, SEQ. ID. No. 13, SEQ. ID. No. 18, SEQ. ID. No. 21, SEQ. ID. No. 24, SEQ. ID. No. 27, or SEQ. ID. No. 30. As above, the invention provides expression vectors and host cells containing the nucleic acids of the invention.

In a preferred embodiment, the isolated nucleic acid molecule encoded a protein having an amino acid sequence corresponding to SEQ. ID. No. 4, SEQ. ID. No. 7, SEQ. ID. No. 11, SEQ. ID. No. 12, SEQ. ID. No. 16, SEQ. ID. No. 17, SEQ. ID. No. 20, SEQ. ID. No. 23, SEQ. ID. No. 26, SEQ. ID. No. 29, or SEQ. ID. No. 32.

Preferred nucleic acid molecules are deoxyribonucleic acid molecules.

The present invention also provides isolated proteins encoded by the accessory gland proteins. Preferred proteins have the amino acid sequences, or fragments thereof, provided in SEQ. ID. No. 4, SEQ. ID. No. 7, SEQ. ID. No. 11, SEQ. ID. No. 12, SEQ. ID. No. 16, SEQ. ID. No. 17, SEQ. ID. No. 20, SEQ. ID. No. 23, SEQ. ID. No. 26, SEQ. ID. No. 29, or SEQ. ID. No. 32.

The present invention provides a gene identified as Acp29AB, its cDNA sequence is as follows (SEQ. ID. No. 5):

```
  1 gacacgcttg aaatcttcca aactggacat gtacgcatct aacctcttat acctgttggc
 61 attatggaac ctttgggatc tcagtggtgg gcagcaggac attccgaacg gaaaggctac
121 attgccaagt ccacaaacgc cgcaaaatac aatcgatcag attggtatta accagaatta
181 ttggtttaca taacgcgc ttaaacaaaa cgaaacattg gcaattattg atacaatgga
241 aatgcgcata gcaagtagct tgctggagtt taaggcccag atggaaatcc agcttcagcc
301 gttaaagatt ataatgcgac accatgcatc caacatcaaa gcgtctaaca acatcaagat
361 gagacgattc gagaaagttg gctccagaca ttttcacatc gagaagaatc taatgcaaac
421 ttggtttgag gcatatgtca catgtcgtaa aatgaacggt catctggcga acatccagga
481 tgagaaggag ctggatggca tcttggcgtt agcacccaac aatagctact ggatagatat
541 atccaaactg gttgaaaatg gcggcacatt cgtctccacc ctaaccggac gagaaccctt
601 ctttgttaaa tggaagagta atcaggatac aaaaaaaaag aatcaatgcg tttacatcta
661 tgctaaagag atgtcctatg atgagtgttt tgaaaaaaaa tctttcgttt gccaagcaga
721 ccagtgggcc taaacataaa gaaatattg ttttgtagct tgaataataa aattataaaa
781 aaaaaaaaaa aa
```

The cDNA encodes an open reading frame which is located at nucleotides 29 to 733 of SEQ. ID. No. 5 (SEQ. ID. No. 6):

```
  1 atgtacgcat ctaacctctt atacctgttg gcattatgga acctttggga tctcagtggt
 61 gggcagcagg acattccgaa cggaaaggct acattgccaa gtccacaaac gccgcaaaat
121 acaatcgatc agattggtat taaccagaat tattggttta catacaacgc gcttaaacaa
181 aacgaaacat tggcaattat tgaccagaat taaatgcgca tagcaagtag cttgccggag
241 tttaaggccc agatggaaat ccagcttcag ccgttaaaga ttataatgcg acaccatgca
301 tccaacatca aagcgtctaa caacatcaag atgagacgat tgagaaagt ggctccaga
361 cattttcaca tcgagaagaa tctaatgcaa acttggtttg aggcatatgt cacatgtcgt
421 aaaatgaacg gtcatctggc gaacatccag gatgagaagg agctggatgg catcttggcg
481 ttagcaccca acaatagcta ctggatagat atatccaaac tggttgaaaa tggcggcaca
541 ttcgtctcca ccctaaccgg acgagaaccc ttctttgtca aacggaagag taatcaggat
601 acaaaaaaaa agaatcaatg cgtttacatc tatgctaaag atgtcta tgatgagtgt
661 tttgaaaaaa aatctttcgt ttgccaagca gaccagtggg cc
```

The amino acid sequence of the Acp29AB protein is provided as follows (SEQ. ID. No. 7):

```
  1 MYASNLLYLL ALWNLWDLSG GQQDIPNGKA TLPSPQTPQN TIDQIGINQN YWFTYNALKQ
 61 NETLAIIDTM EMRIASSLLE FKAQMEIQLQ PLKIIMRHHA SNIKASNNIK MRRFEKVGSR
121 HFHIEKNLMQ TWFEAYVTCR KMNGHLANIQ DEKELDGILA LAPNNSYWID ISKLVENGGT
181 FVSTLTGREP FFVKWKSNQD TKKKNQCVYI YAKEMSYDEC FEKKSFVCQA DQWA
```

The invention further provides a gene encoding an accessory gland protein identified as Acp32CD. The cDNA sequence for Acp32CD is as follows (SEQ. ID. No. 8):

```
   1 cagctgcgct gttgcttcag ctgactgcag caacatggac taacaactgc cactgttttt
  61 cagttcccca gatatgcccc ccttgttgcg gcactgcttt ggacacgcct ttatcggact
 121 gccccttttt aatgggcaag agcagccacg gccacagtca aatcgattcg attccgggca
 181 acggcggtca tctctatata taagggacgg tcggacagcc cgggcagctc agcgttgcag
 241 cgatgtggcg gatgcggatg cggctactca ctggctactt ggtcctgtgg ccctcggcca
 301 actgccggag catggcgctc tgggccagaa gtactacatg aactttgcct tcaataataa
 361 taatccggat ggcgaaggag gcaccggcgt cgatggtggc ggtggtggtg ctggtggtgg
 421 tgccgctggt cccggcggtg gaaccgggga ttcgccccat tcacaagaag gtgacggtag
 481 tgctgcgacg gataacccca atgacgacca cgctacatct gctgataata gtttggctac
 541 tgatggcgat gccattggta agaaggaaag cggcggtggt agcgatggca agagcgactc
 601 caaagactcg agcggaggca atgatgccac gccagcgaat ggtcatgacg atgacaacga
 661 tgacagcgac agaaggatgc caaggatcga caagataagg aagaggaggc cggacaggag
 721 gggaagcgca ccgatcacag ccatcacagt agctacgaga tcagatcgac gacagctttg
 781 gcgggcggta cgtgcggtcc atttacgaga gcagcgagag ccacggacat tcggcagcaa
 841 tgccggctcc aatcagcgga caatgagcc cgtgagagca gtcaggagaa ccaggatgcc
 901 aaggaagtgg ccagcgaagc gcctgctcaa cgggcaggca acgtgccaga tggacccgaa
 961 actggagcca accgggagat ctgaccacag gttcgctcga gggactttgg aagaacacag
1021 acacttcaat tgattttatc attaaaatgc caataaaatt ttaataccaa aaaaaaaaaa
1081 aaaaa
```

Two open reading frames are found within the nucleotide sequence of the Acp32CD cDNA. Open reading frames 1 and 2 are provided as SEQ. ID. Nos. 9 and 10, respectively, as follows:

(SEQ. ID. No. 9)

```
   1 atgccccct tgttgcggca ctgctttgga cacgccttta tcggactgcc ccttttaat
  61 gggcaagagc agccacggcc acagtcaaat cgattcgatt ccgggcaacg gcggtcatct
 121 ctatatataa gggacggtcg gacagcccgg gcagctcagc gttgcagcga tgtggcggat
 181 gcggatgcgg ctactcactg gctacttggt cctgtggccc tcggccaact gccggagcat
 241 ggcgctctgg gccagaagta ctacatgaac tttgccttca acaacaataa tccggatggc
 301 gaaggaggca ccggcgtcga tggtggcggt ggtggtgctg gtggtggtgc cgctggtccc
 361 ggcggtggaa ccggggattc gccccattca caagaaggtg acggtagtgc tgcgacggat
 421 aaccccaatg acgaccacgc tacatctgct gataatagtt tggctactga tggcgatgcc
 481 attggtaaga aggaaagcgg cggtggtagc gatggcaaga gcgactccaa agactcgagc
 541 ggaggcaatg atgccacgcc agcgaatggt catgacgatg acaacgatga cagcgacaga
 601 aggatgccaa ggatcgacaa gataaggaag aggaggccgg acaggagggg aagcgcaccg
 661 atcacagcca tcacagtagc tacgagatca gatcgacgac agctttggcg ggcggtacgt
 721 gcggtccatt tacgagagca gcgagagcca cggacattcg gcagcaatgc cggctccaat
```

-continued
```
781 cagcggacaa tggagcccgt gagagcagtc aggagaacca ggatgccaag gaagtggcca
841 gcgaagcgcc tgctcaacgg gcaggcaacg tgccagatgg acccgaaact ggagccaagg
901 aagatgacta cgaggagatg taacacaacc gggagatctg accacaggtt cgctcgaggg
961 actttggaag aacgcagaca cttcaat
```

(SEQ. ID. No. 10)

```
  1 atgaactttg ccttcaataa taataatccg gatggcgaag gaggcaccgg cgtcgatggt
 61 ggcggtggtg gtgctggtgg tggtgccgct ggtcccggcg gtagaaccgg ggattcgccc
121 cattcacaag aaggtgacgg tagtgctgcg acggataacc ccaatgacga ccacgctaca
181 tctgctgata atagtttggc tactgatggc gatgccattg gtaagaagga aagcggcggt
241 ggtagcgatg gcaagagcga ctccaaagac tcgagcggag gcaatgatgc cacgccagcg
301 aatggtcatg acgatgacaa cgatgacagc gacagaagga tgccaaggat cgacaagata
361 aggaagagga ggccggacag gaggggaagc gcaccgatta cagccatcac agtagctacg
421 agatcagatc gacgacagct ttgtgccggc tccaatcagc ggacaatgga gcccgtgaga
481 gcagtcagga gaaccaggat gccaaggaag tggccagcga agcgcctgct caacgggcag
541 gcaacgtgcc agatggaccc gaaactggag ccaaggaaga tgactacgag gagatgtaac
601 acaaccggga gatctgacca caggttcgct cgagggactt ggaagaacg cagacacttc
661 aat
```

Open reading frame 1, encodes a protein of 269 amino acids. The predicted amino acid sequence from open reading frame 1 of the ACP32CD gene is provided in SEQ. ID. No. 11.:

```
  1 MPPLLRHEFG HAFIGLPLFN GQEQPRPQMN FAFNNNNPDG EGGTGVDGGG GGAGGGAAGP
 61 GGGTGDSPHS QEGDGSAATD NPNDDHATSA DNSLATDGDA IGKKESGGGS DGKSDSKDSS
121 GGNDATPANG HDDDNDDSDR RMPRIDKIRK RRPDRRGSAP ITAITVATRS DRROLWRAVR
181 AVHLREOREP RTFGSNAGSN QRTMEPVRAV RRTRMPRKWP AKRLLNGQAT CQMDPKLEPR
241 KMTTRRCNTT GRSDHRFARG TLEERRHFN
```

Open reading frame 2, encodes a shorter protein lacking the amino terminal 28 amino acids of the protein encoded by open reading frame 1. The predicted amino acid sequence from open reading frame 2 of the ACP32CD gene is provided in SEQ. ID. No. 12:

```
  1 MNFAFNNNNP DGEGGTGVDG GGGGAGGGAA GPGGGTGDSP HSQEGDGSAA TDNPNDDHAT
 61 SADNSLATDG DAIGKKESGG GSDGKSDSKD SSGGNDATPA NGHDDDNDDS DRRMPRIDKI
121 RKRRPDRRGS APITAITVAT RSDRROLWRA VRAVHLREOR EPRTEGSNAG SNQRTMEPVR
181 AVRRTRMPRK WPAKRLLNGQ ATCQMDPKLE PRKMTTRRCN TTGRSDHRFA RGTLEERRHF
```

The present invention also provides a gene encoding an accessory gland protein which is identified as Acp33A (SEQ. ID. No. 13):

```
  1 ggattctaca agatgctacc ttccaagcga gttccatttc ttttcaccat tatcctgttt
 61 ctggctggac tgggtcagca cacaactgaa agtgtacttc cagactgcgt tctttatcca
121 agatgtttga tcacaaagga tccgtgttgc atgtaaagca tctatagaaa tcaaagaagg
181 atcttgtata tggaagtgga aatgtggttc aaaatatcag cacttctcaa ggctgtaaca
241 aaaactgcac tctgttttta taaatacaaa tatccacaaa tatctggtct taacatggca
301 acatttcaag tcttccaata aatcattttc gtttttattg tgaaaaaaaa aaaaaaaaa
361 aaaaaaa
```

Two open reading frames are also found within the nucleotide sequence of the Acp32CD cDNA. Open reading frames 1 and 2 are provided as SEQ. ID. Nos. 14 and 15, respectively, as follows:
(SEQ. ID. No 14)

```
  1 atgctaccct ccaagcgagt tccatttctt ttcaccatta tcctgtttct ggctggactg
 61 ggtcagcaca caactgaaag tgtacttcca gactgcgttc gactgcgttc tttatccaag
121 atgtttga tcacaaagga tccgtgttgc atg
```

(SEQ. ID. No 15)

```
  1 atggaagtgg aaatgtggtt caaaatatca gcacttctca aggctgtaac aaaaactgca
 61 ctctgttttt ataaatacaa atatccacaa atatctggtc ttaacatggc aacatttcaa
121 gtcttccaa
```

Open reading frame 1, encodes a protein of 47 amino acids. The predicted amino acid sequence from open reading frame 1 of the ACP32CD gene is provided in SEQ. ID. No. 16:

1 MLPSKRVPFL FTIILFLAGL GQHTTESVLP DCVLYPRCLI TKDPCCM

Open reading frame 2, encodes a protein of 43 amino acids. The predicted amino acid sequence from open reading frame 2 of the ACP32CD gene is provided in SEQ. ID. No. 17:

1 MEVEMWFKIS ALLKAVTKTA LCFYKYKYPQ ISGLNMATFQ VFQ

The present invention also provides a gene encoding an accessory gland protein which is Acp36DE (SEQ. ID. No. 18):

```
  1 caaatcaaca actaattaat gcacaagacg tgctctcaga caaagatcag aaacagacgc
 61 aagttcagaa caataactta catattcgat tcggtgtgtc agcactaaga gaaggaagaa
121 ataatcctag tttggaaacg atttctcggg ataaagtaga taaaatatca cctgcattgc
181 agttgcaact gttgagatat gcagattctc agtcgcaatc ccagacgcag tcacaatctg
241 cctcacaatc tgaatcaaat gcatcttcac aattccaggc acaggagcaa agcaatcgac
301 tgttgggaaa acccacctgt ttcagaatct cagtcacaat cagagtcaca gtcacagtcc
361 gagtcacaga agcagtcaca gtcgcagtca cagcgacagc aacagataca gacgcaattg
421 caaatactgc gacagttgca acaaaagtca aatgagcaat ctgccgcaca atctgcttct
481 cagattcaat cgcagaggca atcggattct caatccaact tacaattaca agaacaatca
541 caatcgcagt cagagcaagg taagccaatc cagtcacaaa ttcaaattct tcaagggctg
601 cagcaaaaag agttagatga caaatctgca tcacagtcgc agtccgaatc caagacacgg
```

-continued

```
 661 aaagagcaac aaaaacagtt gaatttgcaa caacttgagg agctatcgtc ttcactatca
 721 cagtcacggc tagggctggg acagcaaatc cagtcacagc tacaaaagaa tcagttggat
 781 aagcaatttt cttcacagtt tcagtcacaa tccaagtcac agctggagca acaaatgcaa
 841 ttgcaattac aaagccttcg gcaactgcag cagaagcaat tagatgagca atctgcttca
 901 cagtcgcagc cacagtcaca ggtagcgcaa cagatccagt cacatttgca acttcttcga
 961 ttactgcaat ccagattgaa gacgcagtcg gcattgaaat cagatttaga acaacaaatc
1021 cttttttcaat taaagaaact tacagaagtg caacagaaac agttggctga caacccacc
1081 ttacgaccca gttcaaaatc acaatcgcct gggcagctag agcagcaaat tctgttacac
1141 ctgcaaaatc ttctacactt tcagcagaat cagctaaaat cagatacaca aacccaaagc
1201 cagttgcaag agtcaaaatc taactcactg tcacagtcac agtcacaatc gcaggagcag
1261 ttacagttgc agcgggatca gaatcttcgg caattggaac aagtaaagtt ggaaatgcaa
1321 aatattcgag agctgctgca gaagggcaag tctgagctac aaacccaatc ggactctcag
1381 cgacgtatac atgagctata ccaaaatatt ctgcagctaa ataaggagaa gttgagctac
1441 caattgaaac agttaaaact aaaagaattg gaagaccaaa agaagtcgca ggcagaaata
1501 tcaaagggaa gtaacccatc caatctattt attatcggac aattgccttc cgaaggaaag
1561 ccagctcctg gaaatcaagg tccttcaatt gagcctaagc tggtccccca acccggttca
1621 ctggacaaat tgccatcagg cggagggcta attggcaagc cagcttcaac aggactgtat
1681 attttatcgc cggatttcaa tgatttgtcg gattaccgag atcagtttcg tctacagcaa
1741 gaattaaaaa agcatcaaaa tatattgagc cttttgcagc gtagacaaaa tgataaaaaa
1801 caacaaaacg cacagctgtt gctaggacaa caacagaagg aacaacaagc tcaggaatca
1861 atcaataaac aacagtcctc atctgctggc tctagttctc agaccaagtt acagcaagat
1921 atacaaagta ctggagctca aggctcacag cagggtcttc aagctggatc cactggcctg
1981 cagactagtt ccctacaagg cacagaaagt tctgcatctc aaagcgctct tcagcgattg
2041 aaggagcagg aacaactgcg aattcagacg gaaaatgatc agaaaacctc ttcttcaagc
2101 tcgcacagta actcacaaaa ctcgcagagt tcgtcatcac agtcatcgca ggcatcacag
2161 tctgaagcac aacgacagga ggctggcaat cgaaatacct tgctactaga tcaatcgagc
2221 tccaagactc agtcgagtcg aagtccgagt cgtcgtctca atcatcgtca cattcatcgt
2281 cgcagtcaac gtcgaactca tcttcaaacg ttcaatcgaa actacaagga gaaagccaag
2341 cgctgctaaa caatttgtca ggttaagtag ttaaccttat acttctcaca gtactgacat
2401 gggcgaagag cagccttatt cagatgttaa tcaaaagag gaaataaaat aattgttctt
2461 tcatttaaaa actcgaaaaa aaaaaaaaaa aa
```

An open reading frame encoding the Acp36DE protein is found within the cDNA sequence (SEQ. ID. No. 19):

```
  1 atgcagattc tcagtcgcaa tcccagacgc agtcacaatc tgcctcacaa tctgaatcaa
 61 atgcatcttc acaattccag gcacaggagc aaagcaatcg actgttggga aaacccacct
121 gtttcagaat ctcagtcaca atcagagtca cagtcacagt ccgagtcaca gaagcagtca
181 cagtcgcagt cacagcgaca gcaacagata cagacgcaat tgcaaatact gcgacagttg
241 caacaaaagt caaatgagca atctgccgca caatctgctt ctcagattca atcgcagagg
```

-continued

```
 301 caatcggatt ctcaatccaa cttacaatta caagaacaat cacaatcgca gtcagagcaa
 361 ggtaagccaa tccagtcaca aattcaaatt cttcaagggc tgcagcaaaa agagttagat
 421 gacaaatctg catcacagtc gcagtccgaa tccaagacac ggaaagagca acaaaaacag
 481 ttgaatttgc aacaacttga ggagctatcg tcttcactat cacagtcacg gctagggctg
 541 ggacagcaaa tccagtcaca gctacaaaag aatcagttgg ataagcaatt ttcttcacag
 601 tttcagtcac aatccaagtc acagctggag caacaaatgc aattgcaatt acaaagcctt
 661 cggcaactgc agcagaagca attagatgag caatctgctt cacagtcgca gccacagtca
 721 caggtagcgc aacagatcca gtcacatttg caacttcttc gattactgca atccagattg
 781 aagacgcagt cggcattgaa atcagattta gaacaacaaa tcctttttca attaaagaaa
 841 cttacagaag tgcaacagaa acagttggct gagcaaccca ccttacgacc cagttcaaaa
 901 tcacaatcgc ctgggcagct agagcagcaa attctgttac acctgcaaaa tcttctacac
 961 tttcagcaga atcagctaaa atcagataca caacccaaa gccagttgca agagtcaaaa
1021 tctaactcac tgtcacagtc acagtcacaa tcgcaggagc agttacagtt gcagcgggat
1081 cagaatcttc ggcaattgga acaagtaaag ttggaaatgc aaaatattcg agagctgctg
1141 cagaagggca agtctgagct acaaacccaa tcggactctc agcgacgtat acatgagcta
1201 taccaaaata ttctgcagct aaataaggag aagttgagct accaattgaa acagttaaaa
1261 ctaaaagaat tggaagacca aaagaagtcg caggcagaaa tatcaaaggg aagtaaccca
1321 tccaatctat ttattatcgg acaattgcct tccgaaggaa agccagctcc tggaaatcaa
1381 ggtccttcaa ttgagcctaa gctggtcccc caacccggtt cactggacaa attgccatca
1441 ggcggagggc taattggcaa gccagcttca acaggactgt atattttatc gccggatttc
1501 aatgatttgt cggattaccg agatcagttt cgtctacagc aagaattaaa aaagcatcaa
1561 aatatattga gccttttgca gcgtagacaa aatgataaaa acaacaaaa cgcacagctg
1621 ttgctaggac aacaacagaa ggaacaacaa gctcaggaat caatcaataa acaacagtcc
1681 tcatctgctg gctctagttc tcagaccaag ttacagcaag atatacaaag tactggagct
1741 caaggctcac agcagggtct tcaagctgga tccactggcc tgcagactag ttccctacaa
1801 ggcacagaaa gttctgcatc tcaaagcgct cttcagcgat tgaaggagca ggaacaactg
1861 cgaattcaga cggaaaatga tcagaaaacc tcttcttcaa gctcgcacag taactcacaa
1921 aactcgcaga gttcgtcatc acagtcatcg caggcatcac agtctgaagc acaacgacag
1981 gaggctggca atcgaaatac cttgctacta gatcaatcga gctccaagac tcagtcgagt
2041 cgaagtccga gtcgtcgtct caatcatcgt cacattcatc gtcgcagtca acgtcgaact
2101 catcttcaaa cgttcaatcg aaactacaag gagaaagcca agcgctgc
```

The predicted amino acid sequence of the Acp36DE protein is as follows (SEQ. ID. No. 20):

```
  1 MQILSRNPRR SHNLPHNLNQ MHLHNSRHRS KAIDCWENPP VSESQSQSES QSQSESQKQS
 61 QSQSQRQQQI QTQLQILRQL QQKSNEQSAA QSASQIQSQR QSDSQSNLQL QEQSQSQSEQ
121 GKPIQSQIQI LQGLQQKELD DKSASQSQSE SKTRKEQQKQ LNLQQLEELS SSLSQSRLGL
181 GQQIQSQLQK NQLDKQFSSQ FQSQSKSQLE QQMQLQLQSL RQLQQKQLDE QSASQSQPQS
241 QVAQQIQSHL QLLRLLQSRL KTQSALKSDL EQQILFQLKK LTEVQQKQLA EQPTLRPSSK
301 SQSPGQLEQQ ILLHLQNLLH FQQNQLKSDT QTQSQLQESK SNSLSQSQSQ SQEQLQLQRD
```

```
-continued
361 QNLRQLEQVK LEMQNIRELL QKGKSELQTQ SDSQRRIHEL YQNILQLNKE KLSYQLKQLK

421 LKELEDQKKS QAEISKGSNP SNLFIIGQLP SEGKPAPGNQ GPSIEPKLVP QPGSLDKLPS

481 GGGLIGKPAS TGLYILSPDF NDLSDYRDQF RLQQELKKHQ NILSLLQRRQ NDKKQQNAQL

541 LLGQQQKEQQ AQESINKQQS SSAGSSSQTK LQQDIQSTGA QGSQQGLQAG STGLQTSSLQ

601 GTESSASQSA LQRLKEQEQL RIQTENDQKT SSSSSHSNSQ NSQSSSSQSS QASQSEAQRQ

661 EAGNRNTLLL DQSSSKTQSS RSPSRRLNHR HIHRRSQRRT HLQTFNRNYK EKAKRC
```

The present invention provides a gene encoding an accessory gland protein which is Acp53Ea (SEQ. ID. No. 21):

```
  1 ccgaaagcac acagataagg cttccaatga aactgataaa ggttacacta gtgttcagct 61 tactggctct cgtatttgtg gcccaaacgg aggcgcaaaa tccaatatgg gagaattggc 121 tggcatgcaa tagaattggt actaaagcgc ttgccagtct gctgagagaa acaattccaa 181 ccgttcgtaa tttactgaac tgcattgact tcaatccacc aaccgatatt ggaaatagtt 241 acctttcaaa acttaagtta tactatgagc ttgttaagcg aggtgcgctt gacaagactc 301 agtgtctgat tgtgccactc aaggaatcag tgagactact gaggcctta gtaaaatcgc 361 ttgagaccaa caaatgcttg ggtgaataaa tcactatttt ggccatagta aaataaattt 421 ctgagcatta ataaagcacg
```

An open reading frame encoding the Acp53Ea protein is found within the cDNA sequence (SEQ. ID. No. 22):

```
  1 atgaaactga taaaggttac actagtgttc agcttactgg ctctcgtatt tgtggcccaa 61 acggaggcgc aaaatccaat atgggagaat tggctggcat gcaatagaat tggtactaaa 121 gcgcttgcca gtctgctgag agaaacaatt ccaaccgttc gtaatttact gaactgcatt 181 gacttcaatc caccaaccga tattggaaat agttaccttt caaaacttaa gttatactat 241 gagcttgtta agcgaggtgc gcttgacaag actcagtgtc tgattgtgcc actcaaggaa 301 tcagtgagac tactgaggcc ttatgtaaaa tcgcttgaga ccaacaaatg cttgggtgaa
```

The predicted amino acid sequence of the Acp53Ea protein is as follows (SEQ. ID. No. 23):

```
  1 MKLIKVTLVF SLLALVFVAQ TEAQNPIWEN WLACNRIGTK ALASLLRETI PTVRNLLNCI

61 DFNPPTDIGN SYLSKLKLYY ELVKRGALDK TQCLIVPLKE SVRLLRPYVK SLETNKCLGE
```

The present invention provides a gene encoding an accessory gland protein which is identified as Acp63F (SEQ. ID. No. 24):

```
  1 ctttgcaaga tgaaagctat catcgttttt attctgttca tttcaagtgt gcatgctatg 61 agcaaatgca accaagcaat ttatctaaat cttgatcctc actgcggaat acttcccgat 121 tgtaacttag atggtccaaa tccaagttac ctcaataggg tgtcgtgtga acgcaaagaa 181 aacgaaaaac caggattcat cgaactaatt cccggaaaat gtctccatgg taaaccgcgt 241 tgctcgttaa aatagtaata ttgttccaat atttccatgc atatatgttt caattaaagg 301 cattataaat acctataaaa aaa
```

An open reading frame encoding the Acp63F protein is found within the cDNA sequence (SEQ. ID. No. 25):

```
  1 atgaaagcta tcatcgtttt tattctgttc atttcaagtg tgcatgctat gagcaaatgc
 61 aaccaagcaa tttatctaaa tcttgatcct cactgcggaa tacttcccga ttgtaactta
121 gatggtccaa atccaagtta cctcaatagg gtgtcgtgtg aacgcaaaga aaacggaaaa
181 ccaggattca tcgaactaat tcccggaaaa tgtctccatg gtaaaccgcg ttgctcgtta
241 aaa
```

The predicted amino acid sequence of the Acp63F protein is as follows (SEQ. ID. No. 26):

```
  1 MKAIIVFILF ISSVHAMSKC NQAIYLNLDP HCGILPDCNL DGPNPSYLNR VSCERKENGK
 61 PGFIELIPGK CLHGKPRCSL K
```

The present invention provides a gene encoding an accessory gland protein which is identified as Acp76A (SEQ. ID. No. 27):

```
   1 atatcaagct tatgactctt ggataagcca ttgatatagc aattgtaaat atattatgtg
  61 caattctcct tattttctaa gacattctta ataatataat gcgaactaag gttacattcc
 121 atctgcgcat gcgtgagtcc ttttgctcag caggaacgaa agtacaacgg gtcgtatgag
 181 ttatggcaat cgaatgggca cacgtggccg ccggtccaat ggccagtaaa tcaaactttt
 241 tggcagggcg agtaaacagt gttataaatc agaaaaccgc aaggcagcca ccaggcagct
 301 accatattgt ccatggagga aagcagacag ttggcagact taagtcggac gaaaagacat
 361 ccacccacgc gggcggattg caatgtgcca ggatgcaagt gacgcatagt gctattaaca
 421 tattaccagg cggtaagtgg gtggataaca cattcagtcg gtggatggaa gtacgtgcat
 481 agaacataga gctgccagtg aatattggag caattggagc actgggtgct aaatatgagc
 541 acttgatgaa aacataacac tgactaaaca agatatttct ctgcggctga atttatctag
 601 cgaaagtgtg aaattgttgt tgatttatgt tatactaagc acgccatata tatgaggtgg
 661 cgaatttacg acgatttact aagatttttaa tgtactcttc cttggttaga ggatagaaag
 721 catgaaattg aatagcagtg caataaatcc gtactaattt ccattcgttt ttgcgtatta
 781 tccaatatct taagggtcat tccccttgtg tgtatatata ggaacaaagt aagtttaaga
 841 agctcattgc ggctttggaa aatgggcaac catcaagtaa cattcttagt actgtgcacg
 901 tcgctcctct ttcaaaatac aatacaacaa aatgtatcat ttcaactgat aagggaaatc
 961 gatagataca caccagagaa ttttgtacta tcagtgttga atatagaaat gattctttt
1021 gagatccatg ccgctaaggc agttgaaagt aataacgatt tggaaggag cttgatcata
1081 aactttggat actccgaagc aaggcaggaa gtactggatt ggggattgag atataagaaa
1141 gcctcgagcg ccaagttcca gatggccaac aaggtggcag tgtctcagaa actgcccta
1201 tcgcaaaagc tgcgtctggt aaacgaggtg ctgatgacga gcgccaagaa gtatgatgta
1261 acaaaggatg tcagaccatc aaaattaatg gatgaatggt tgtcctccca tttggatggt
1321 gtactcgcca attttgtaca agagaagaag ttaaacgcgg gcgaaaacat tgtagccatc
1381 agcggaatga cagtcactcc cctttgggca tctcatttcc aatcagagat taatagatac
1441 tttgtcaata atcctggcac tggatatgct tcgaaagacc caacatgtgt gcccatgatg
```

```
-continued
1501 cactcattgt cctcgtttga aaccatgtcc acggacgagg ccaaaggtat atacattcca 1561 ttctcatcgg caaacttggg tatgttgatc ctcctgccga ggaaaggtgt cacctgcaag 1621 gacattttgg ataatttaaa caaccagatc aatgtggaat ataatgatca caaggatgtt 1681 cacttgctac tgcccatatt caaggagaaa tttgactaca atattgccaa attctttaac 1741 ggaattaaca ttgaagacac gtttaaagat cggcgttta aatcgaaagc caaaatcaaa 1801 atcaacaact tccgagtcaa ccatggcata cgatttcaac ccattctccg tttagaagta 1861 gttgatgata ttaatactgg aaagaccgaa acgtttgaag taaatcgccc atttgtcttt 1921 gtcataaagg ataaggttaa cgtatacgca gttggtcgaa ttgaaaacct agatggactt 1981 actgacaaag tgaattgctc caagaaatac gctgatctca agtcgtaaaa tatccataat 2041 atatttcgaa gcataataaa gcaagaaaat ataaaaaaaa aaaaaaaaa aa
```

An open reading frame encoding the Acp76A protein is found within the cDNA sequence (SEQ. ID. No. 28):

```
  1 atgggcaacc atcaagtaac attcttagta ctgtgcacgt cgctcctctt tcaaaataca 61 atacaacaaa atgtatcatt tcaactgata agggaaatcg atagatacac accagagaat 121 tttgtactat cagtgttgaa tatagaaatg attcttttg agatccatgc cgctaaggca 181 gttgaaagta ataacgattt ggaaaggagc ttgatcataa actttggata ctccgaagca 241 aggcaggaag tactggattg gggattgaga tataagaaag cctcgagcgc caagttccag 301 atggccaaca aggtggcagt gtctcagaaa ctgcccctat cgcaaaagct gcgtctggta 361 aacgaggtgc tgatgacgag cgccaagaag tatgatgtaa caaaggatgt cagaccatca 421 aaattaatgg atgaatggtt gtcctcccat ttggatggtg tactcgccaa ttttgtacaa 481 gagaagaagt taaacgcggg cgaaaacatt gtagccatca gcggaatgac agtcactccc 541 ctttgggcat ctcatttcca atcagagatt aatagatact tgtcaataa tcctggcact 601 ggatatgctt cgaaagaccc aacatgtgtg cccatgatgc actcattgtc ctcgtttgaa 661 accatgtcca cggacgaggc caaaggtata tacattccat ctcatcggc aaacttgggt 721 atgttgatcc tcctgccgag gaaaggtgtc acctgcaagg acattttgga taatttaaac 781 aaccagatca atgtggaata taatgatcac aaggatgttc acttgctact gcccatattc 841 aaggagaaat ttgactacaa tattgccaaa ttctttaacg gaattaacat tgaagacacg 901 tttaaagatt cggcgtttaa atcgaaagcc aaaatcaaaa tcaacaactt ccgagtcaac 961 catggcatac gatttcaacc cattctccgt ttagaagtag ttgatgatat taatactgga 1021 aagaccgaaa cgtttgaagt aaatcgccca tttgtctttg tcataaagga taaggttaac 1081 gtatacgcag ttggtcgaat tgaaaaccta gatggactta ctgacaaagt gaattgctcc 1141 aagaaatacg ctgatctcaa gtcg
```

The predicted amino acid sequence of the Acp76A protein is as follows (SEQ. ID. No. 29):

```
  1 MGNHQVTFLV LCTSLLFQNT IQQNVSFQLI REIDRYTPEN FVLSVLNIEM ILFEIHAAKA

61 VESNNDLERS LIINFGYSEA RQEVLDWGLR YKKASSAKFQ MANKVAVSQK LPLSQKLRLV

121 NEVLMTSAKK YDVTKDVRPS KLMDEWLSSH LDGVLANFVQ EKKLNAGENI VAISGMTVTP

181 LWASHFQSEI NRYFVNNPGT GYASKDPTCV PMMHSLSSFE TMSTDEAKGI YIPFSSANLG
```

-continued

```
241 MLILLPRKGV TCKDILDNLN NQINVEYNDH KDVHLLLPIF KEKFDYNIAK FFNGINIEDT

301 FKDSAFKSKA KIKINNFRVN HGIRFQPILR LEVVDDINTG KTETFEVNRP FVFVIKDKVN

361 VYAVGRIENL DGLTDKVNCS KKYADLKS
```

The present invention provides a gene encoding an accessory gland protein which is identified as Acp98AB (SEQ. ID. No. 30):

```
  1 atggaattcc ctaatcctgt tcttagaaga gcagcaggac attccgaacg gaaaggctac 61 acacactatc aaaggatgac gaggatgtcc aagtgaatca ccagctaaag caaggatatt 121 atgtatatct aaggaaatca aataaacttg catgctctaa aaa
```

An open reading frame encoding the Acp98AB protein is found within the cDNA sequence (SEQ. ID. No. 31):

```
  1 atggaattcc ctaatcctgt tcttagccgc attgggcgca gcctccgcac gaataagggg 61 acacactatC aaaggatgac gaggatgtcc aag
```

The predicted amino acid sequence of the Acp98AB protein is as follows (SEQ. ID. No. 32):
1 MEFPNPVLSR IGRSLRTNKG THYQRMTRMS K The present invention also provides a method for determining whether a female *Drosophila melanogaster* has recently mated. An antibody, fragment thereof, or probe which recognizes an acessory protein, including those proteins described in SEQ. ID. No. 4, SEQ. ID. No. 7, SEQ. ID. No. 11, SEQ. ID. No. 12, SEQ. ID. No. 16, SEQ. ID. No. 17, SEQ. ID. No. 20, SEQ. ID. No. 23, SEQ. ID. No. 26, SEQ. ID. No. 29, and SEQ. ID. No. 32, is used to identify the presence of the accessory gland protein in the female after mating. The antibody, fragment thereof, or probe is bound to a label so that it is effective to permit detection of the protein upon binding of the antibody to the protein. The labeled antibody is contacted with a fluid or tissue sample from the female *Drosophila melanogaster* under conditions effective to permit binding of the antibody to the protein. The presence of any of protein in the biological sample by is determined by detecting the label.

EXAMPLES

Example 1

Materials and Methods
Fly Handling and Rearing

Wild type Canton S or Oregon R *D. melanogaster* were maintained on yeast-glucose media at room temperature. Unmated animals were anesthetized with $CO_2$ and collected within 10 hours of eclosion. Flies were kept in fresh vials isolated from the opposite sex until dissected or quick-frozen prior to RNA extraction.
Isolation of New Accessory Gland Genes.

By minor modifications of procedures described in DiBenedetto (1987), 32P-labeled cDNAs were prepared from the poly A+ RNA of 2-day-old adult female Canton S flies and, separately, from accessory glands (attached to ejaculatory ducts) that had been dissected from 2-day-old adult male Canton S flies. These cDNAs were hybridized to duplicate sets of filters containing a total of 22,000 clones of genomic DNA in Charon 4A (Maniatis, 1978). One set of filters received $1.2 \times 10^7$ cpm of labeled cDNA from male reproductive tissues. Prior to incubation with the filters this cDNA was prehybridized with 20 ug of polyA+ RNA from adult females; the female RNA competitor was left in during the filter hybridization. The second set of filters received 1.2×107 cpm of female-derived cDNA, without competitor.

39 clones that consistently showed strong (or exclusive) hybridization to the male tissue probe but not to the female tissue probe through three sequential rounds of plaque purification and screening were retained for further study. These clones were then screened for hybridization to RNAs from accessory glands, or ejaculatory ducts, or testes, or the remainder of the male, or whole adult females. A clone is defined as encoding an accessory gland-specific transcript if that RNA is present in accessory glands but not in any of the other RNA sources listed above. Twenty clones fell into this category. By screening these 20 clones for hybridization to previously cloned accessory gland genes, six re-isolates of the genomic region encoding Acp95EF were found (DiBenedetto, 1987; DiBenedetto, 1990). The remaining 14 clones corresponded to previously-unreported Acp genes. Of these clones, three encompassed overlapping segments of genomic DNA encoding Acp33A; the remaining 11 were single isolates.
Nucleic Acids The fragment(s) of each genomic clone homologous to the male RNA were identified by Northern and "reverse Northern" strategies. Those fragments were used as probes to isolate cDNA clones from male adult *Drosophila melanogaster* libraries (Poole, 1985; Monsma and Wolfner, 1988). Routine nucleic acid manipulations including cloning and subcloning into Bluescript vectors (Stratagene), restriction mapping, Southern blotting, determination of transcriptional orientation, DNA sequencing by the dideoxy chain termination method (Sanger, 1977), and isolation of overlapping genomic clones for Acp36DE were done essentially as in Maniatis (1978) and Ausubel (1994). RNA preparation, Northern blotting and hybridizations in situ to polytene chromosomes were by slight modifications of methods described in DiBenedetto (1987). When needed, sequences from multiple clones of a given Acp were aligned to obtain the complete sequence of the open reading frame. In four instances (Acps 32CD, 33A, 76A and 98AB) the cDNA clone was incomplete and lacked the start of the open reading frame and/or any untranslated leader region. Since our focus is on the protein encoded by the Acp gene, RACE-PCR and/or sequencing of genomic DNA immediately 5' to the first base of the cDNA clone was used to obtain the full open reading frame. This analysis did not extend to defining the starting nucleotide of the Acp mRNA; thus lengths of 5' UTRs given in FIG. 1 are minimal sizes. Sequences were analyzed with GCG sequence analysis software, and have been submitted to GenBank. Accession numbers are given in FIG. 1.

Whole-mount in situ Hybridization

Accessory glands were dissected in PBS and treated essentially as in Lehmann and Tautz (1994), except that PBS was used rather than PBST, pretreated the tissue in 50 ug/ml of proteinase K followed by incubation in 2 mg/ml glycine in PBS-Triton, and eliminated heparin from the hybridization buffer. Hybridization and detection with a digoxigenin-labeled probe (Genius Kit, Boehringer Mannheim) was by minor modification of the procedures in Tautz and Pfeifle (1989). Stained accessory glands were mounted on slides in 25% glycerol and photographed using a Zeiss Axioskop and Kodak Gold 200 film.

Example 2

New Genes Encoding Accessory Gland Proteins (Acps)

In differential cDNA hybridization screens, 12 independent new genes were identified (FIG. 1). The genomic clones were restriction-mapped, and their fragment(s) that hybridized to the accessory gland-specific transcript were determined. On Southern blots of genomic DNA, 11 of the genes showed hybridization patterns consistent with single copy genes. All but one of these genes hybridized in situ to a single polytene band; the exception was Acp33A, which showed aminor second site of hybridization at 32E. Each gene's chromosomal position is included in the gene's name in accordance with *Drosophila melanogaster* nomenclature rules. Two genes, Acp53Ea and Acp53Eb, are derived from polytene band 53E. However they are distinct, non cross-hybridizing genes whose immediate chromosomal regions do not overlap. The genomic clones containing Acp genes did not hybridize to any other male-limited transcripts. However, some of the genomic clones contained regions that hybridized additionally to sex-nonspecific or female-specific transcripts.

The twelfth gene detected in the screens, Acp rep1, had characteristics of a moderately-repetitive gene. Acp rep1 probes hybridized to multiple bands on genomic Southern blots and multiple polytene loci upon in situ hybridization. This gene was not studied further.

On the basis of their chromosomal positions and/or hybridization, these new genes do not correspond to any of the previously-reported *D. melanogaster* Acp genes identified in hybridization screens or from purified accessory gland peptides (Schäfer, 1986; DiBenedetto, 1987; Chen, 1988; Monsma and Wolfner, 1988; Simmerl, 1995). One of the 11 unique genes, Acp36DE, may correspond to a previously-identified locus, AcpC, which was detected via a natural variant lacking a protein band of ~125–128 kDa on SDS polyacrylamide gels of accessory gland proteins (Whalen and Wilson, 1986). As described below, Acp36DE encodes a protein of a predicted molecular weight of 81.3 kDa. However, the protein's sequence contains a large number of potential and actual (Bertram, 1996) glycosylation sites, and antibodies against Acp36DE recognize a 122 kDa glycoprotein (Bertram, 1996). Unfortunately, the AcpC variant strains reported by Whalen and Wilson (1986) were no longer extant when Acp36DE was discovered, so it is impossible to determine whether AcpC corresponds to Acp36DE. The approximate genetic map position of one other Acp gene reported by Whalen and Wilson (1986), AcpB, is near Acps 29AB, 31F and 32CD. The other two positions reported by Whalen and Wilson (1986) do not correspond to sites of any of the Acp genes identified.

Thus, 19 non-repetitive Acp genes have been cloned (Schäfer, 1986; DiBenedetto, 1987; Chen, 1988; Monsma and Wolfner, 1988; Simmerl, 1995; and this study). These genes represent 16 independent chromosomal regions; 26A and 57D contain clusters of two (Acp26Aa,b; Monsma and Wolfner, 1988) and three (57Da,b,c; Simmerl, 1995) unrelated Acp genes, respectively.

Interestingly, the new nonrepetitive Acp genes are all autosomal. So are all four Acp genes or gene clusters isolated in previous screens that were unbiased as to chromosomal position (Schäfer, 1986; DiBenedetto, 1987; Chen, 1988). Given that the X chromosome represents about 20% of the genome, the probability that all 15 Acp gene regions would fall outside the X is $(0.8)15$, which equals 0.035. Even making worst-case assumptions about the library screened (Maniatis, 1978), like its containing no overlapping clones and its deriving from DNA of a 50-50 mixture of XX and XY embryos, it is calculated that $p=0.076$, which is highly suggestive of nonrandom placement of Acp genes. The absence of Acp genes from the X chromosome might relate to their male-limited expression. In *D. melanogaster* males, autosomal genes are present in two copies per cell whereas X-linked genes occur in only one copy per cell. Dosage compensation increases the transcription of non sex-specific X-linked genes in male cells so that their transcript levels are equivalent to those produced by two copies of the gene female cells (reviewed in Kelley and Kuroda, 1995). It may be that autosomal placement of Acp genes was advantageous since the genes could be expressed at high levels without also needing to acquire dosage compensation regulation.

Acp genes were first isolated in screens for male-specific transcripts (Schäfer, 1986; DiBenedetto, 1987). Not surprisingly, the screen reported here, with its enriched probe used in the presence of RNA competitor, was 10-fold more efficient than the earlier screens in detecting Acp genes. Considering that from this screen 10 genes were isolated singly, three independent isolates of one were obtained, and six were presumed independent isolates of another, a rough estimate of the number of Acp genes that can be isolated by this type of screen can be made. Since one cannot assume equal representation of all sequences in the library, Bunge and Fitzpatrick (1993) recommend using the method of Esty (1986) for this estimate, even though this estimator is associated with large standard deviations. This estimator [$c^\wedge=c/(1-(c1/n))$; Esty, 1986] predicts the existence of 25.3 Acp genes detectable by our screening procedures. The method of Good (1950) predicts about 19 Acp genes detectable by the present procedures. This method assumes all genes are equally represented in the library, based on estimates of "coverage" as defined by Bunge and Fitzpatrick (1993). The Good method tends to yield an underestimate if the assumption of complete coverage is not met. Though these are rough estimates, both calculations suggest that the Acp genes isolated in differential screens performed here and by others represent more than half the genes that could be isolated in such screens, which will fail to detect rare RNAs or Acp genes flanked by highly-expressed non sex-specific transcription units.

Example 3

Expression of the New Acps

Northern blot analysis was performed with each of the Acp genes; an example of the results is shown in FIG. 2A. All the genes with the exception of Acp31F encode single accessory gland-specific transcripts. The transcripts fell into three size classes. Two genes encoded transcripts larger than 2 kb, four encoded mRNAs between 0.95 and 2 kb, and six encoded RNAs smaller than 0.75 kb. The sizes of the transcripts are listed in FIG. 1.

To determine the type of accessory gland cells in which these transcripts are produced, digoxigenin-labeled DNA probes complementary to the transcripts of Acps 29AB, 31F, 33A, 36DE, 53Ea, 63F, 76A or 98AB were hybridized in situ to RNA in whole mount accessory glands. In all cases, the probes hybridized strongly to mRNA in main cells (e.g. FIG. 2B for Acp36DE). In most cases the strong staining of main cells made it impossible to determine unambiguously whether there was also staining in the secondary cells. In the case of Acp36DE an accessory gland fortuitously positioned so that secondary cells were visible at the edge of the lobe was observed. In that case, it was possible to determine that the secondary cells were unstained (FIG. 2B, inset). Gene expression in main cells is stimulated in response to mating (Schmidt, 1985; DiBenedetto, 1990; Monsma, 1990; Bertram, 1992; Simmerl, 1995). This stimulation is also observed for the one new gene tested, Acp36DE (Bertram, 1994).

Example 4

General Features of the Predicted New Acps

The goal in isolating new Acp genes was to identify new molecules that could ultimately be correlated with the functions of the accessory gland. Therefore, the sequence of the predicted proteins encoded by 9 of the new genes was determined.

Of the two Acp genes with large transcripts, the one with the simpler transcription pattern, Acp36DE, was selected for sequence analysis. cDNAs were sequenced from all the smaller Acp transcripts for which cDNA clones were cloned (Acps 29AB, 33A, 32CD, 53Ea, 62F, 63F, 76A, 98AB). FIG. 3 reports the open reading frame sequence of each Acp, with FIG. 1 giving some of the salient numerical characteristics of the transcript and its open reading frame. In all cases but two, only a single long open reading frame in the Acp gene's transcript, beginning at the most 5' AUG of the mRNA, was found. The two exceptions were Acps 33A and 36DE. The former encodes two open reading frames of similar size and codon bias; it is not known which (or if both) is the bona fide Acp ORF. For Acp36DE, the first AUG initiates a short open reading frame of 18 amino acids upstream of a 716 amino acid open reading frame. Antibodies raised against the protein predicted by the long open reading frame confirm that it is the expressed Acp (Bertram, 1996). As shown in FIG. 1, 4 bases prior to the initiating AUGs of all the Acp genes listed showed only partial matches to consensus for translational initiation in *Drosophila* (C/A A A C/A; Cavener, 1987). No consensus in these bases was seen among Acp genes.

Several features are apparent in the new predicted Acps (FIG. 3). First, all except Acp36DE contain predicted secretion signals. A sequence that matches a consensus for signal sequence cleavage (von Heijne, 1983) is found at the positions indicated in FIG. 3. Consistent with this observation, all Acps tested (29AB, 32CD, 53Ea, 62F, 63F and 98AB; Y.O.L., U.T. and M.F.W. unpublished, and 76A; Coleman, 1995) are secreted and transferred to females during mating. Despite its lack of an apparent signal sequence, Acp36DE is also secreted and transferred to females (Bertram, 1996). The predicted stretch of hydrophobic residues at its N-terminus may function as a secretion signal.

The second feature of the predicted Acps is that many contain sequences that suggest they may be subject to post-translational modifications such as cleavage, amidation and glycosylation. Basic amino acids in contexts favorable for cleavage to liberate peptide hormones from a precursor molecule are found in Acps 29AB, 32CD, 36DE, 53Ea, and 76A. Park and Wolfner (1995) have shown that cleavage of Acp26Aa occurs at sites consistent with the use of basic amino acids in such contexts (Schwartz, 1986; Benoit, 1987; Nakayama, 1992). Acp32CD contains a potential amidation site (I73GKK; Kreil, 1984; Bradbury and Smyth, 1987). Acps 29AB, 32CD, 36DE, 53Ea, 62F, 63F and 76A contain sites for potential glycosylation (Kornfeld and Kornfeld, 1985; Miletich and Broze, 1990). The case of Acp36DE is particularly remarkable: in addition to a site for N-linked glycosylation (Asn439-Pro-Ser) and in fact being N-glycosylated (Bertram, 1996), Acp36DE contains large amounts of serine and threonine, at which O-linked glycosylation could occur. These residues are mostly concentrated in four regions: amino acids 42–64, 92–118, 334–351 and 591–665 of this glutamine-rich protein. Acp36DE also contains, along with Acps 32CD and 62F, sequences matching consensus for glycosaminoglycan attachment sites (Hassell, 1986; Bourdon, 1987), suggesting that these proteins could become associated with, or part of, an extracellular matrix. Taken together, these features suggest that the new Acps are secreted molecules, and some have the potential to be cleaved to smaller peptides and/or be glycosylated. The Acps that do not contain cleavage sites (Acps 33A, 62F 63F, 98AB) are within the size range of known secreted accessory gland peptides (e.g. Chen, 1988; Monsma and Wolfner, 1988) and thus might be synthesized and secreted without further modification.

Example 5

Intriguing Sequence Similarities in Two Predicted Acps

The databases were searched for sequences that might have similarities to the 9 new predicted Acps. Two showed sequence similarity to proteins in the data bases (FIGS. 3,4).

Acp76A: A search of protein databases reveals that the 11 amino acids starting at position 345 and ending at 355, FEVNRPFVFVI (SEQ. ID. No. 33), are a perfect match to the serpin signature sequence, [LIVMF]-X-[LIVMFA]-[DNQ]-[RKHQ]-[PS]-F-[LIVMFY]-2X-[LIVMF] (SEQ. ID. No. 34) (Henikoff and Henikoff, 1994). This amino acid sequence similarity places the Acp76A in the serpin (serine protease inhibitors) superfamily of proteins. Members of this superfamily include alpha-1-antitrypsin, angiotensinogen, ovalbumin, antiplasmin, placental plasminogen activator inhibitor, thyroxin binding protein, and heparin cofactor II (Carrell and Boswell, 1986; Kanost, 1989). Many members of the serpin superfamily are extracellular serine protease inhibitors, helping to control proteolytic events associated with a wide variety of regulated biochemical pathways (Carrell and Boswell, 1986; Gettins, 1992; Zou, 1994). Several mammalian proteins in the serpin superfamily play roles in blood coagulation. Others are involved in fibrinolysis, inflammation, and tumor suppression. In humans a serpin, Protein C Inhibitor (PCI), is present in semen and interacts with at least three different proteases: urokinase plasminogen activator, tissue-type plasminogen activator, and prostate specific antigen (Espana, 1993). The physiological role of these interactions in human semen is unknown.

Although it is not yet known whether Acp76A, with its perfect serpin signature, is an active protease inhibitor, there are indications that protease inhibitors could play a critical role in controlling Acp function in *D. melanogaster*. Regulated proteolysis is a hallmark of Acp26Aa's fate in mated female flies (Monsma, 1990; Park and Wolfner, 1995). Acp36DE is also converted to a smaller form upon transfer to females (Bertram, 1996). Acp26Aa remains intact in the male's reproductive tract. It undergoes ordered proteolysis in the genital tract of the mated female, due to a combination of seminal fluid components donated by the male as well as components donated by the female (Park and Wolfner, 1995). It is possible that the protease(s) that cleaves Acp26Aa is made by the male's accessory gland, but is kept in check in the gland by protease inhibitors such as, potentially, Acp76A or the protease inhibitor found in *D. funebris* accessory glands (Schmidt, 1989). Upon transfer to the female, the protease inhibitor(s) would be inactivated, allowing the protease(s) to become active and to cleave Acp26Aa.

A second possible role for a protease inhibitor derived from accessory glands is in the coagulation of semen after mating. In *Drosophila*, as in many other insects, a mating plug consisting of coagulated semen forms in the mated female's uterus. The plug is thought to facilitate the storage of sperm by the female (Lefevre and Jonsson, 1962; Fowler, 1973; Bertram, 1996). By analogy to the role of members of the serpin superfamily in the tightly regulated proteolytic cascades that cause blood clotting in mammals (Gettins, 1992; Espana, 1993; Potempa, 1994), a serpin, potentially Acp76A, could function to regulate proteolytic cleavage events crucial to the formation of the mating plug. Consistent with this suggestion, Acp76A is transferred to the female fly during mating, and the majority of the transferred Acp76A is found in the mating plug when it is expelled from the female between 2–4 hours after mating (Coleman, 1995).

Acp62F: Acp62F has a 28 amino acid region of sequence similarity with several small neurotoxins made by the Brazilian "armed" spider, *Phoneutria nigriventer*. Sequence similarity is highest to the 48 amino acid toxin PhTx2-6, one of several related neurotoxins in the PhTx2 fraction of the *P. nigriventer* venom (Rezende, 1991; Cordeiro, 1992; Cordeiro, 1995). Optimal alignment of the Acp62F and PhTx2-6 sequences (FIG. 4) shows a 51.7% identity, 82.7% similarity in a region of 28 amino acid residues (aas 46–73) of Acp62F to a 27 amino acid region of PhTx2-6. In this alignment, all six of Acp62F's cysteines in this region are perfectly aligned with 6 of the 10 cysteines in PhTx2-6 and the other PhTx2 toxins. Furthermore, a seventh cysteine at the N-terminus of Acp62F is only 3 residues away from a corresponding cysteine in PhTx2-6.

PhTx2 toxins inhibit the closure of voltage-gated sodium channels in frog muscles in vitro, thus prolonging action potentials and increasing membrane excitability (Araujo, 1993; Cordeiro, 1995). If the sequence similarity observed between Acp62F and PhTx2-6 reflects a functional similarity, it could suggest roles for Acp62F in neuromuscular events following mating. Such roles could include opening the entry to the sperm storage organs to facilitate efficient storage of transferred sperm or removal of previously stored sperm, delaying movement of the first egg through the oviduct to allow sperm time to be stored before being pushed out by the egg or, alternatively, facilitating rapid release of eggs following mating.

The toxin-similarity of Acp62F is also intriguing in light of the demonstrated toxicity of *D. melanogaster* seminal fluid to mated female flies (Chapman, 1995; Rice, 1996). Acp62F enters the hemolymph after its entry into the mated *Drosophila* female. Since injection of toxin PhTx2-6 into the hemolymph of house flies is lethal (Rezende, 1991; Cordeiro, 1995), it is plausible that hemolymph entry of Acp62F could contribute to the decreased lifespan of mated female *D. melanogaster* (Fowler and Partridge, 1989; Chapman, 1995). Toxicity of seminal fluid is suggested to be an unintended negative consequence of a seminal fluid component that has a reproductively advantageous function (Chapman, 1995; Keller, 1995; Chapman and Partridge, 1996). Future genetic analysis of Acp62F is needed to determine whether this protein plays such a Jekyll-and-Hyde role.

Example 6

Lethality of Acp62F Expressed from a Baculovirus Vector in *Trichoplusia ni*

The survival of $5^{th}$ instar *Trichoplusia ni* was monitored after injection with a baculovirus vector carrying the gene encoding Acp62F. The gene encoding Acp62F was cloned into the BacPac vector from Clontech. This vector allows for the introduction and expression of the cloned gene in insect cells. *Trichoplusia ni* larva were injected with the baculovirus after reaching the $5^{th}$ instar stage of development. Two control groups were maintained, uninfected larva and vector injected larva. Survival was monitored at 2, 2.5, and 3 days post injection. The results shown in FIG. 5 were normalized relative to the survival of the control larva. A significant decrease in larval survival was seen with all the larva infected with baculovirus vectors carrying the Acp62 gene.

Example 7

Lethality of Acp62F Protein in *Trichoplusia ni*

Acp62F was injected into larvae at the $3^{rd}$ instar stage of development. Survival was monitored over a 12.5 day period after injection. Larvae were injected with 115 nanograms of Acp62F. Control larvae were injected with an equal molar amount of BSA or an equal volume of saline solution. The percentage of surviving caterpillars was determined daily. The results are shown in FIG. 6. The percentage of caterpillars which pupated is also reported in Table 1. The percentage of pupating animals is virtually identical to the survival of the larva after 12.5 days. The injection of Acp62F protein clearly has an effect on the survival of the caterpillars. However, it may not be as effective as the introduction of a baculovirus which can continually express the protein due the half-life of the protein.

TABLE 1

Pupation of *Trichoplusia ni* After Injection With Acp62F Protein
% Pupation

| | | |
|---|---|---|
| Uninjected | n = 24 | 95.8% |
| Saline | n = 38 | 94.9% |
| BSA | n = 56 | 98.2% |
| 62FH6 | n = 55 | 78.2% |

Example 8

Expression of Acp62F is Lethal to Pre-Adult Fruit Flies

The effect of accessory gland proteins on survival of pre-adult fruit flies was determined by inducing the expression of an accessory gland protein at different stages in the development of fruit fly larva. A fruit fly which is heterozygous for an accessory gland protein gene under the control of a heat inducible promoter was bred with a wild-type fly. The resulting progeny were expected to be 50% wild-type and 50% carriers of the heat inducible accessory gland protein gene. This allowed for cultures of flies with otherwise identical genetic makeup and at the identical developmental stage. Cultures were heat shocked on a particular day of development and then the flies were allowed to grow up (except for the group identified as "all," which was heat shocked every day through the first 9 days of development). Normally 80–90% of eggs produced flies. A similar ratio of eggs developed into flies for those flies which were produced from flies carrying the Acp 26Aa, 29AB, 32CD, 33A, 53E, 63F/64A, and 92EF accessory gland protein genes (See FIG. 7).

On the other hand, only half as many flies resulted from eggs produced from a fly carrying an inducible Acp62F gene. Furthermore, when the flies were examined it was determined that the homozygous wild-type flies survived at the expected rates, but that few or no flies expressing the Acp62F gene had survived.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES

The following references, which have been cited above, are hereby incorporated by reference:

Araujo, D. A. M., Cordeiro, M. N., C. R., D. and Beirao, P. S. L. (1993) Effects of a toxic fraction, PhTx2, from the spider *Phoneutria nigriventer* on the sodium current. Arch. Pharmacol. 347, 205–208.

Ausubel, F. M., Brent, R., Kingston, R. E., Moore, D. D., Seidman, J. G., Smith, J. A. and Struhl, K. (1994) Current Protocols in Molecular Biology. John Wiley and Sons. Inc.

Benoit, R., Ling, N. and Esch, T. (1987) A new prosomatostatin-derived peptide reveals a pattern for prohormone cleavage at monobasic sites. Science. 238, 1126–1129.

Bertram, M., Akerkar, G. A., Ard, R. L., Gonzalez, C. and Wolfner, M. F. (1992) Cell type specific gene expression in the *Drosophila melanogaster* male accessory gland. Mechs. Dev. 38, 33–40.

Bertram, M. J. (1994). Cell type-specific gene expression in the *Drosophila melanogaster* male accessory gland and the characterization of an accessory gland protein. Ph. D. thesis, Cornell University, Ithaca N.Y.

Bertram, M. J., Neubaum, D. M. and Wolfner, M. F. (1996) Localization of the *Drosophila* accessory gland protein Acp36DE in the mated female suggests a role in sperm storage. Ins. Bioch. Mol. Biol. 26, 971–980.

Bourdon, M. A., Krusius, T., Campbell, S., Schwartz, N. B. and Ruoslahti, E. (1987) Identification and synthesis of a recognition signal for the attachment of glycosaminoglycans to proteins. Proc. Natl. Acad. Sci. USA. 84, 3194–3198.

Bradbury, A. F. and Smyth, D. G. (1987) Biosynthesis of the C-terminal amide in peptide hormones. Biosci. Rep. 7, 907–916.

Bunge, J. and Fitzpatrick, M. (1993) Estimating the number of species: a review. J. Amer. Stats. Assoc. 88, 364–373.

Carrell, R. W. and Boswell, D. R. (1986). Serpins: a family of serine protease inhibitors. in Proteinase Inhibitors. New York, Elsevier. 403–420.

Cavener, D. R. (1987) Comparison of the consensus sequence flanking translational start sites in *Drosophila* and vertebrates. Nucl. Acids Res. 15, 1353–1361.

Chapman, T., Liddle, L. F., Kalb, J. M., Wolfner, M. F. and Partridge, L. (1995) Cost of mating in *Drosophila melanogaster* females is mediated by male accessory gland products. Nature. 373, 241–244.

Chapman, T. and Partridge, L. (1996) Sexual conflict as fuel for evolution. Nature. 381, 189–190.

Chen, P. S. (1991) Biochemistry and molecular regulation of the male accessory gland secretions in *Drosophila* (Diptera). Annls. Soc. ent. Fr. 27, 231–244.

Chen, P. S. (1996) The accessory gland proteins in male *Drosophila*: structural, reproductive and evolutionary aspects. Experientia. 52, 503–510.

Chen, P. S., Stumm-Zollinger, E., Aigaki, T., Balmer, J., Bienz, M. and Bohlen, P. (1988) A male accessory gland peptide that regulates reproductive behavior of female *D. melanogaster*. Cell. 54, 291–298.

Coleman, S., Drahn, B., Petersen, G., Stolorov, J. and Kraus, K. (1995) A *Drosophila* male accessory gland protein that is a member of the serpin superfamily of proteinase inhibitors is transferred to females during mating. Ins. Bioch. Mol. Biol. 25, 203–207.

Cordeiro, M., Diniz, C. R., Valentim, A. and Richardson, M. (1992) The purification and amino acid sequences of four Tx2 neurotoxins from the venom of the Brazilian "armed" spider *Phoneutria nigriventer*. FEBS Lett. 310, 153–156.

Cordeiro, M., Richardson, M., Gilroy, J., Gomes de Figuereido, S., Beirao, P. S. L. and Diniz, C. R. (1995) Properties of the venom from the South American "armed" spider *Phoneutria nigriventer*. J. Toxicol.-Toxin Rev. 14, 309–326.

Coulthart, M. B. and Singh, R. S. (1988) Differing amounts of genetic polymorphism in testes and male accessory glands of *Drosophila melanogaster* and *Drosophila simulans*. Bioch. Genet. 26, 153–164.

DiBenedetto, A. J., Harada, H. A. and Wolfner, M. F. (1990) Structure, cell-specific expression, and mating-induced regulation of a *Drosophila melanogaster* male accessory gland gene. Dev. Biol. 139, 134–148.

DiBenedetto, A. J., Lakich, D. M., Kruger, W. D., Belote, J. M., Baker, B. S. and Wolfner, M. F. (1987) Sequences expressed sex-specifically in *Drosophila melanogaster* adults. Dev. Biol. 119, 242–251.

Espana, F., Estelles, A., Fernandez, P. J., Giilabert, J., Sanchez-Cuenca, J. and Griffin, H. (1993) Evidence for the regulation of urokinase and tissue type plasminogen activators by the serpin, protein c inhibitor, in semen and blood plasma. Thromb. and Haem. 70, 989–994.

Esty, W. W. (1986) Estimation of the size of a coinage: a survey and comprison of methods. Numis. Chron. 146, 185–215.

Fowler, G. L. (1973) Some aspects of the reproductive biology of *Drosophila*: sperm transfer, sperm storage and sperm utilization. Adv. Genet. 17, 293–360.

Fowler, K. and Partridge, L. (1989) A cost of mating in female fruitflies. Nature. 338, 760–761.

Gettins, P., Patston, P. A. and Shapira, M. (1992) Structure and mechanism of action of serpins. Hemat./Onc. Clin. of N. Amer. 6, 1393–1408.

Goding, (1983) Monoclonal Antibodies: Principles and Practice, pp. 98–118, New York:Academic Press.

Goding, J., (1983) Monoclonal Antibodies: Principles and Practice, pp. 98–118 (N.Y. Academic press).

Good, I. J. (1950). Probability and the weighing of evidence. London, Charles Griffin.

Hall, J. C. (1994) The mating of a fly. Science. 264, 1702–1714.

E. Harlow, et. al., editors, Antibodies: A Laboratory Manual (1988).

Hassell, J. R., Kimura, J. H. and Hascall, V. C. (1986) Proteoglycan core protein families. Ann. Rev. Bioch. 55, 539–567.

Henikoff, S. and Henikoff, J. G. (1994) Protein family classification based on searching a database of blocks. Genomics. 19, 97–107.

Herndon, L. A. and Wolfner, M. F. (1995) A *Drosophila* seminal fluid protein, Acp26Aa, stimulates egg-laying in females for one day following mating. Proc. Natl. Acad. Sci. USA. 92, 10114–10118.

Ingman-Baker, J. and Candido, E. P. M. (1980) Proteins of the *Drosophila melanogaster* male reproductive system: two-dimensional gel patterns of proteins synthesized in XO, XY and XYY testis and paragonial gland and evidence that the Y chromosome does not code for structural sperm proteins. Biochem. Genet. 18, 809–828.

Kanost, M. R., Sarvamangala, V. P. and Wells, M. A. (1989) Primary structure of a member of the serpin superfamily of proteinase inhibitors from an insect, Manduca sexta. J. Biol. Chem. 264, 965.

Keller, L. (1995) All's fair when love is war. Nature. 373, 190–191.

Kelley, R. L. and Kuroda, M. I. (1995) Equality for X chromosomes. Science. 270, 1607–1610.

Kitts, P. A. and Possee, R. D. (1993) A Method for Producing Recombinant Baculovirus Expression Vectors at High Frequency. BioTechniques 14, 810–817

Kitts, P. A., Ayres, M. D., and Possee, R. D. (1990) Linearization of Baculovirus DNA Enhances the Recovery of Recombinant Virus Expression Vectors. Nuc. Acid. Res. 18, 5667–5672.

Kohler, G. and Milstein, C. (1975) Continuous Cultures of Fused Cells Secreting Antibody of Predefined Specificity. Nature 256, 495–497.

Kohler, G. and Milstein, C. (1976) Derivation of Specific Antibody-Producing Tissue Culture and Tumor Lines by Cell Fusion. Eur. J. Immunol. 6, 511–519.

Kornfeld, R. and Kornfeld, S. (1985) Assembly of asparagine-linked oligosaccharides. Ann. Rev. Biochem. 54, 631–664.

Kreil, G. (1984) Occurrence, detection and biosynthesis of carboxy-terminal amides. Meth. Enzymol. 106, 218–223.

Kubli, E. (1996) The *Drosophila* sex-peptide: a peptide pheromone involved in reproduction. Adv. Devel. Biochem. 4, 99–128.

Lehmann, R. and Tautz, D. (1994) In situ hybridization to RNA. in Meth. Cell Biol. 44: *Drosophila melanogaster*: practical uses in cell and molecular biology. L. S. B. Goldstein and E. A. Fyrberg, eds. Academic Press, San Diego Calif. pp. 575–598.

Lefevre, G. and Jonsson, V. B. (1962) Sperm transfer, storage, displacement and utilization in *Drosophila melanogaster*. Genetics. 47, 1719–1736.

Luckow, V. A. and Summers, M. D. (1989) High Level Expression of Nonfused Foreign Genes with *Autographa californica* Nuclear Polyhedrosis Virus Expression Vectors. Virol. 17, 31–39.

Maniatis, T., Hardison, R. C., Lacy, E., Lauer, J., O'Connell, C., Quon, D., Sim, G. K. and Efstradiatis, A. (1978) The isolation of structural genes from libraries of eukaryotic DNA. Cell. 15, 687–701.

Miletich, J. P. and Broze, G. J. J. (1990) Beta protein C is not glycosylated at asparagine 329; the rate of translation may influence the usage at asparagine-X-cysteine sites. J. Biol. Chem. 265, 11397–11404.

Monsma, S. A., Harada, H. A. and Wolfner, M. F. (1990) Synthesis of two *Drosophila* male accessory gland proteins and their fate after transfer to the female during mating. Dev. Biol. 142, 465–475.

Monsma, S. A. and Wolfner, M. F. (1988) Structure and expression of a *Drosophila* male accessory gland gene whose product resembles a peptide pheromone precursor. Genes Dev. 2, 1063–1073.

Nakayama, K., Watanabe, T., Nakagawa, T., Kim, W. S., Nagahama, M., Hosaka, M., Hatsuzawa, K., Kondoh-Hashiba, K. and Murakami, K. (1992) Consensus sequence for precursor processing of mono-arginyl sites: evidence for the involvement of a kex2-like endoprotease in precursor cleavages at both dibasic and mono-arginyl sites. J. Biol. Chem. 267, 16335–16340.

Ohashi, Y. Y., Hamo-Fukushima, K. and Fuyama, Y. (1991) Purification and characterization of an ovulation stimulating substance from the male accessory glands of *Drosophila suzukii*. Insect Biochem. 21, 413–419.

Park, M. and Wolfner, M. F. (1995) Male and female cooperate in the processing of a *Drosophila melanogaster* seminal fluid protein. Dev. Biol. 171, 694–702.

Poole, S. J., Kauvar, L. M., Drees, B. and Komberg, T. (1985) The engrailed locus of *Drosophila*: Structure analysis of an embryonic transcript. Cell. 40, 37–43.

Potempa, J., Korzus, E. and Travis, J. (1994) The serpin superfamily of proteinase inhibitors: Structure, function, and regulation. J. Biol. Chem. 269, 15957–15960.

Radka, S. F., Kostyu, D. D. and Amos, D. B. (1982) A Monoclonal Antibody Directed Against the HLA-Bw6 Epitope. J. Immunol. 128, 2804–2806.

Radka, S. F., Amos, D. B., Quackenbush, L. J., and Cresswell, P. (1984) HLA-DR7-Specific Monoclonal Antibodies and a Chimpanzee Anti-DR7 Serum Detect Different Epitopes on the Same Molecule. Immunogenetics 19, 63–76.

Rezende, L. J., Cordeiro, M. N., Oliveira, E. B. and Diniz, C. R. (1991) Isolation of neurotoxic peptides from the venom of the "armed" spider, *Phoneutria nigriventer*. Toxicon. 29, 1225–1233.

Rice, W. R. (1996) Sexually antagonistic male adaptation triggered by experimental arrest of female evolution. Nature. 381, 232–234.

Roberts, T. M. and Lauer, G. D. (1979) Maximizing Gene Expression on a Plasmid Using Recombination in Vitro. Methods in Enzymology, 68, 473–482.

Sambrook, (1989) Molecular Cloning: A Laboratory Manual, Cold Springs Laboratory, Cold Springs Harbor, N.Y.

Sanger, F., Nicklen, S. and Coulson, A. R. (1977) DNA sequencing with chain terminating inhibitors. Proc. Natl. Acad. Sci. USA. 74, 5463–5467.

Schäfer, U. (1986) Genes for male-specific transcripts in *Drosophila melanogaster*. Mol. Gen. Genet. 202, 219–225.

Schmidt, T., Choffat, Y., Schneider, M., Hunziker, P., Fuyama, Y. and Kubli, E. (1993) *Drosophila suzukii* contains a peptide homologous to the *Drosophila melanogaster* sex peptide and functional in both species. Ins. Bioch. Mol. Biol. 23, 571–579.

Schmidt, T., Stumm-Zollinger, E. and Chen, P. S. (1985) Protein metabolism of *Drosophila melanogaster* male accessory glands—III. Stimulation of protein synthesis following copulation. Insect Biochem. 15, 391–401.

Schmidt, T., Sturnm-Zollinger, E. and Chen, P. S. (1989) A male accessory gland peptide with protease inhibitory activity in *Drosophila funebris*. J. Biol. Chem. 264, 9745–9749.

Schwartz, T. W. (1986) The processing of peptide precursors: proline-directed arginyl cleavage and other monobasic processing mechanisms. FEBS Lett. 200, 1–10.

Simmerl, E., Schäfer, M. and Schäfer, U. (1995) Structure and regulation of a gene cluster for male accessory gland transcripts in *Drosophila melanogaster*. Ins. Biochem. Molec. Biol. 25, 127–137.

Smith, G. E., Summers, M. D., and Fraser, M. J. (1983) Production of Human Beta Interferon in Insect Cells Infected with a Baculovirus Expression Vector. Mol. Cell. Biol. 3, 2156–2165.

"Stratagene Cloning Systems" Catalog (1993) from Stratagene, La Jolla, Calif.

Studier, F. W. et. al., (1990) "Use of T7 RNA Polymerase to Direct Expression of Cloned Genes," Gene Expression Technology vol. 185.

Stumm-Zollinger, E. and Chen, P. S. (1985) Protein metabolism of *Drosophila* male accessory glands: I. Characterization of secretory proteins. Ins. Bioch. 15, 375–383.

Summers and Smith, Texas Agricultural Experiment Station Bulletin No. 1555 (1987).

Tautz, D. and Pfeifle, C. (1989) A non-radioactive in situ hybridization method for the localization of specific RNAs in *Drosophila* embryos reveals translational control of the segmentation gene hunchback. Chromosoma. 98, 81–85.

von Heijne, G. (1983) Patterns of amino acids near signal sequence cleavage sites. Eur. J. Biochem. 135, 17–21.

Whalen, M. and Wilson, T. G. (1986) Variation and genomic localization of genes encoding *Drosophila melanogaster* male accessory gland proteins separated by sodium dodecyl sulfate-polyacrylamide gel electrophoresis. Genetics. 114, 77–92.

Wolfner, M. F. (1997) Tokens of love: functions and regulation of *Drosophila* male accessory gland products. Ins. Bioch. Mol. Biol. 27, 179–192.

Zou, Z., Anisowicz, A., Hendrix, M. J. C., Thor, A., Neveu, M., Sheng, S., Rafidi, K., Seftor, E. and Sager (1994) Maspin, a serpin with tumor-suppressing activity in human mammary epithelial cells. Science. 263, 526–529.

What is claimed is:

1. An isolated nucleic acid molecule encoding an accessory gland protein from *Drosophila* which has the biological property of an insect toxin.

2. The isolated nucleic acid molecule according to claim 1, wherein the nucleic acid molecule is selected from the group consisting of:
   a nucleic acid molecule having a nucleotide sequence according to SEQ ID NO:2; or
   a nucleic acid molecule whose complement hybridizes to a nucleic acid molecule comprising the nucleotide sequence of SEQ ID NO:2 under hybridization conditions comprising hybridization in 0.9M SSC buffer at a temperature of 37° C. and washing with the SSC buffer at 37° C.

3. The isolated nucleic acid molecule according to claim 1, wherein the accessory gland protein has greater than 40% sequence indentify to SEQ ID NO:35.

4. The isolated nucleic acid molecule according to claim 1, wherein the accessory gland protein is toxic to *Drosophila* or caterpillar.

5. An expression vector comprising the nucleic acid molecule according to claim 1.

6. The expression vector according to claim 5, wherein the expression vector is a viral vector.

7. The expression vector according to claim 6, wherein the viral vector is a baculovirus vector.

8. A host cell comprising the expression vector according to claim 5.

9. The host cell according to claim 8, wherein the host cell is an insect cell.

10. The isolated nucleic acid molecule according to claim 2, wherein the accessory gland protein is toxic to *Drosophila* or caterpillar.

11. An expression vector comprising the nucleic acid molecule according to claim 2.

12. The expression vector according to claim 11, wherein the expression vector is a viral vector.

13. The expression vector according to claim 12, wherein the viral vector is a baculovirus vector.

14. A host cell comprising the expression vector according to claim 11.

15. The host cell according to claim 14, wherein the host cell is an insect cell.

16. An isolated nucleic acid molecule encoding a protein which has the biological activity of an insect toxin, wherein said nucleic acid molecule is selected from the group consisting of:
   a nucleic acid molecule encoding a protein having the amino acid sequence of SEQ ID NO:4;
   a nucleic acid molecule having a nucleotide sequence selected from the group consisting of SEQ ID NO:2 and SEQ ID NO:3; and
   a nucleic acid molecule whose complement hybridizes to a nucleic acid molecule having the nucleotide sequence selected from the group consisting of SEQ ID NO:2 and SEQ ID NO:3, under hybridization conditions comprising hybridization in 0.9M SSC buffer at a temperature of 37° C. and washing with the SSC buffer at 37° C.

17. An isolated nucleic acid molecule according to claim 16, wherein the isolated nucleic acid molecule encodes a protein having the amino acid sequence corresponding to SEQ ID NO:4.

18. An isolated nucleic acid molecule according to claim 16, wherein the nucleic acid molecule is a deoxyribonucleic acid molecule.

19. An expression vector comprising the nucleic acid molecule according to claim 16.

20. The expression vector according to claim 19, wherein the expression vector is a viral vector.

21. The expression vector according to claim 20, wherein the viral vector is a baculovirus vector.

22. A host cell comprising the expression vector according to claim 19.

23. The host cell according to claim 22, wherein the host cell is an insect cell.

* * * * *

SEQUENCE LISTING

<160> NUMBER OF SEQ ID NOS: 35

<210> SEQ ID NO 1
<211> LENGTH: 88
<212> TYPE: PRT
<213> ORGANISM: Drosophila melanogaster

<400> SEQUENCE: 1

```
Met Pro Pro Leu Leu Arg His Cys Phe Gly His Ala Phe Ile Gly Leu
 1               5                  10                  15

Pro Leu Phe Asn Gly Gln Glu Gln Pro Arg Pro Gln Ser Asn Arg Phe
            20                  25                  30

Asp Ser Gly Gln Arg Arg Ser Ser Leu Tyr Ile Arg Asp Gly Arg Thr
        35                  40                  45

Ala Arg Ala Ala Gln Arg Cys Ser Asp Val Ala Asp Ala Asp Ala Ala
    50                  55                  60

Thr His Trp Leu Leu Gly Pro Val Ala Leu Gly Gln Leu Pro Glu His
65                  70                  75                  80

Gly Ala Leu Gly Gln Lys Tyr Tyr
                85
```

-continued

<210> SEQ ID NO 2
<211> LENGTH: 439
<212> TYPE: DNA
<213> ORGANISM: Drosophila melanogaster

<400> SEQUENCE: 2

```
ggtagacgta ttccccatct acaatgacgg acatgtggag cttgaagatc tgtgcctgtc    60
tgggccttct attactttc aaacccatcg actccatggg atggcaagga cctaaagttg   120
actgtacggc caacggaact cagacggagt gtcctgtagc atgtcctgaa acctgcgagt   180
actccggcaa tggaccctgc gtcaagatgt gcggagctcc ttgtgtgtgt aagccgggat   240
atgttatcaa tgagaggatt ccggcctgtg ttctgcgatc cgattgccca aaagatgttg   300
ttcgaaagga agatatgcta ctgggtgtat cgaactttaa gtgctttagc agaaattaca   360
actgttcata gaaatttatt aggaaggcag ctaaacttta aactaaaata caataaaatg   420
taaataaaaa aaaaaaaaa                                               439
```

<210> SEQ ID NO 3
<211> LENGTH: 345
<212> TYPE: DNA
<213> ORGANISM: Drosophila melanogaster

<400> SEQUENCE: 3

```
atgacggaca tgtggagctt gaagatctgt gcctgtctgg gccttctatt acttttcaaa    60
cccatcgact ccatgggatg gcaaggacct aaagttgact gtacggccaa cggaactcag   120
acggagtgtc ctgtagcatg tcctgaaacc tgcgagtact ccggcaatgg accctgcgtc   180
aagatgtgcg gagctccttg tgtgtgtaag ccgggatatg ttatcaatga gaggattccg   240
gcctgtgttc tgcgatccga ttgcccaaaa gatgttgttc gaaaggaaga tatgctactg   300
ggtgtatcga actttaagtg ctttagcaga aattacaact gttca                  345
```

<210> SEQ ID NO 4
<211> LENGTH: 115
<212> TYPE: PRT
<213> ORGANISM: Drosophila melanogaster

<400> SEQUENCE: 4

```
Met Thr Asp Met Trp Ser Leu Lys Ile Cys Ala Cys Leu Gly Leu Leu
  1               5                  10                  15
Leu Leu Phe Lys Pro Ile Asp Ser Met Gly Trp Gln Gly Pro Lys Val
             20                  25                  30
Asp Cys Thr Ala Asn Gly Thr Gln Thr Glu Cys Pro Val Ala Cys Pro
         35                  40                  45
Glu Thr Cys Glu Tyr Ser Gly Asn Gly Pro Cys Val Lys Met Cys Gly
     50                  55                  60
Ala Pro Cys Val Cys Lys Pro Gly Tyr Val Ile Asn Glu Arg Ile Pro
 65                  70                  75                  80
Ala Cys Val Leu Arg Ser Asp Cys Pro Lys Asp Val Val Arg Lys Glu
                 85                  90                  95
Asp Met Leu Leu Gly Val Ser Asn Phe Lys Cys Phe Ser Arg Asn Tyr
            100                 105                 110
Asn Cys Ser
        115
```

<210> SEQ ID NO 5
<211> LENGTH: 792

<210> SEQ ID NO 5
<211> LENGTH: 792
<212> TYPE: DNA
<213> ORGANISM: Drosophila melanogaster

<400> SEQUENCE: 5

| | | |
|---|---|---|
| gacacgcttg aaatcttcca aactggacat gtacgcatct aacctcttat acctgttggc | 60 |
| attatggaac ctttgggatc tcagtggtgg gcagcaggac attccgaacg gaaaggctac | 120 |
| attgccaagt ccacaaacgc cgcaaaatac aatcgatcag attggtatta accagaatta | 180 |
| ttggtttaca tacaacgcgc ttaaacaaaa cgaaacattg gcaattattg atacaatgga | 240 |
| aatgcgcata gcaagtagct tgctggagtt taaggcccag atggaaatcc agcttcagcc | 300 |
| gttaaagatt ataatgcgac accatgcatc caacatcaaa gcgtctaaca acatcaagat | 360 |
| gagacgattc gagaaagttg gctccagaca ttttcacatc gagaagaatc taatgcaaac | 420 |
| ttggtttgag gcatatgtca catgtcgtaa aatgaacggt catctggcga acatccagga | 480 |
| tgagaaggag ctggatggca tcttggcgtt agcacccaac aatagctact ggatagatat | 540 |
| atccaaactg gttgaaaatg gcggcacatt cgtctccacc ctaaccggac gagaacccct | 600 |
| ctttgttaaa tggaagagta atcaggatac aaaaaaaaag aatcaatgcg tttacatcta | 660 |
| tgctaaagag atgtcctatg atgagtgttt tgaaaaaaaa tctttcgttt gccaagcaga | 720 |
| ccagtgggcc taaacataaa gaaaatattg ttttgtagct tgaataataa aattataaaa | 780 |
| aaaaaaaaaa aa | 792 |

<210> SEQ ID NO 6
<211> LENGTH: 701
<212> TYPE: DNA
<213> ORGANISM: Drosophila melanogaster

<400> SEQUENCE: 6

| | | |
|---|---|---|
| atgtacgcat ctaacctctt atacctgttg gcattatgga acctttggga tctcagtggt | 60 |
| gggcagcagg acattccgaa cggaaaggct acattgccaa gtccacaaac gccgcaaaat | 120 |
| acaatcgatc agattggtat taaccagaat tattggttta catacaacgc gcttaaacaa | 180 |
| aacgaaacat tggcaattat tgaccagaat taaatgcgca tagcaagtag cttgccggag | 240 |
| tttaaggccc agatggaaat ccagcttcag ccgttaaaga ttataatgcg acaccatgca | 300 |
| tccaacatca aagcgtctaa caacatcaag atgagacgat tgagaaagtt ggctccagac | 360 |
| attttcacat cgagaagaat ctaatgcaaa cttggtttga ggcatatgtc acatgtcgta | 420 |
| aaatgaacgg tcatctggcg aacatccagg atgagaagga gctggatggc atcttggcgt | 480 |
| tagcacccaa caatagctac tggatagata tatccaaact ggttgaaaat ggcggcacat | 540 |
| tcgtctccac cctaaccgga cgagaaccct ctttgtcaa acggaagagt aatcaggata | 600 |
| caaaaaaaaa gaatcaatgc gtttacatct atgctaaaga gatgtcctat gatgagtgtt | 660 |
| ttgaaaaaaa atctttcgtt tgccaagcag accagtgggc c | 701 |

<210> SEQ ID NO 7
<211> LENGTH: 234
<212> TYPE: PRT
<213> ORGANISM: Drosophila melanogaster

<400> SEQUENCE: 7

Met Tyr Ala Ser Asn Leu Leu Tyr Leu Leu Ala Leu Trp Asn Leu Trp
1               5                   10                  15
Asp Leu Ser Gly Gly Gln Gln Asp Ile Pro Asn Gly Lys Ala Thr Leu
            20                  25                  30

```
Pro Ser Pro Gln Thr Pro Gln Asn Thr Ile Asp Gln Ile Gly Ile Asn
         35                  40                  45
Gln Asn Tyr Trp Phe Thr Tyr Asn Ala Leu Lys Gln Asn Glu Thr Leu
     50                  55                  60
Ala Ile Ile Asp Thr Met Glu Met Arg Ile Ala Ser Ser Leu Leu Glu
 65                  70                  75                  80
Phe Lys Ala Gln Met Glu Ile Gln Leu Gln Pro Leu Lys Ile Ile Met
                 85                  90                  95
Arg His His Ala Ser Asn Ile Lys Ala Ser Asn Ile Lys Met Arg
                100                 105                 110
Arg Phe Glu Lys Val Gly Ser Arg His Phe His Ile Glu Lys Asn Leu
            115                 120                 125
Met Gln Thr Trp Phe Glu Ala Tyr Val Thr Cys Arg Lys Met Asn Gly
        130                 135                 140
His Leu Ala Asn Ile Gln Asp Glu Lys Glu Leu Asp Gly Ile Leu Ala
145                 150                 155                 160
Leu Ala Pro Asn Asn Ser Tyr Trp Ile Asp Ile Ser Lys Leu Val Glu
                165                 170                 175
Asn Gly Gly Thr Phe Val Ser Thr Leu Thr Gly Arg Glu Pro Phe Phe
            180                 185                 190
Val Lys Trp Lys Ser Asn Gln Asp Thr Lys Lys Asn Gln Cys Val
        195                 200                 205
Tyr Ile Tyr Ala Lys Glu Met Ser Tyr Asp Glu Cys Phe Glu Lys Lys
    210                 215                 220
Ser Phe Val Cys Gln Ala Asp Gln Trp Ala
225                 230

<210> SEQ ID NO 8
<211> LENGTH: 1085
<212> TYPE: DNA
<213> ORGANISM: Drosophila melanogaster

<400> SEQUENCE: 8
cagctgcgct gttgcttcag ctgactgcag caacatggac taacaactgc cactgttttt      60
cagttcccca gatatgcccc ccttgttgcg gcactgcttt ggacacgcct ttatcggact     120
gccccttttt aatgggcaag agcagccacg gccacagtca atcgattcg  attccgggca     180
acggcggtca tctctatata taagggacgg tcggacagcc cgggcagctc agcgttgcag     240
cgatgtggcg gatgcggatg cggctactca ctggctactt ggtcctgtgg ccctcggcca     300
actgccggag catggcgctc tgggccagaa gtactacatg aactttgcct tcaataataa     360
taatccggat ggcgaaggag gcaccggcgt cgatggtggc ggtggtggtg ctggtggtgg     420
tgccgctggt cccggcggtg aaccgggga ttcgccccat tcacaagaag gtgacggtag      480
tgctgcgacg gataacccca atgacgacca cgctacatct gctgataata gtttggctac     540
tgatggcgat gccattggta agaaggaaag cggcggtggt agcgatggca agagcgactc     600
caaagactcg agcggaggca atgatgccac gccagcgaat ggtcatgacg atgacaacga     660
tgacagcgac agaaggatgc caaggatcga caagataagg aagaggaggc cggacaggag     720
gggaagcgca ccgatcacag ccatcacagt agctacgaga tcagatcgac gacagctttg     780
gcgggcggta cgtgcggtcc atttacgaga gcagcgagag ccacggacat tcggcagcaa     840
tgccggctcc aatcagcgga caatggagcc cgtgagagca gtcaggagaa ccaggatgcc     900
aaggaagtgg ccagcgaagc gcctgctcaa cgggcaggca acgtgccaga tggacccgaa     960
```

```
actggagcca accgggagat ctgaccacag gttcgctcga gggactttgg aagaacacag    1020
acacttcaat tgattttatc attaaaatgc caataaaatt ttaataccaa aaaaaaaaaa    1080
aaaaa                                                                1085
```

<210> SEQ ID NO 9
<211> LENGTH: 987
<212> TYPE: DNA
<213> ORGANISM: Drosophila melanogaster

<400> SEQUENCE: 9

```
atgcccccct tgttgcggca ctgctttgga cacgccttta tcggactgcc ccttttaat      60 gggcaagagc agccacggcc acagtcaaat cgattcgatt ccgggcaacg gcggtcatct    120
ctatatataa gggacggtcg gacagcccgg gcagctcagc gttgcagcga tgtggcggat    180
gcggatgcgg ctactcactg gctacttggt cctgtggccc tcggccaact gccggagcat    240
ggcgctctgg ccagaagta ctacatgaac tttgccttca acaacaataa tccggatggc     300
gaaggaggca ccggcgtcga tggtggcggt ggtggtgctg gtggtggtgc cgctggtccc    360
ggcggtggaa ccggggattc gccccattca caagaaggtg acggtagtgc tgcgacggat    420
aaccccaatg acgaccacgc tacatctgct gataatagtt tggctactga tggcgatgcc    480
attggtaaga aggaaagcgg cggtggtagc gatggcaaga gcgactccaa agactcgagc    540
ggaggcaatg atgccacgcc agcgaatggt catgacgatg acaacgatga cagcgacaga    600
aggatgccaa ggatcgacaa gataaggaag aggaggccgg acaggagggg aagcgcaccg    660
atcacagcca tcacagtagc tacgagatca gatcgacgac agctttggcg gcggtacgt     720 gcggtccatt tacgagagca gcgagagcca cggacattcg gcagcaatgc cggctccaat    780
cagcggacaa tggagcccgt gagagcagtc aggagaacca ggatgccaag gaagtggcca    840
gcgaagcgcc tgctcaacgg gcaggcaacg tgccagatgg acccgaaact ggagccaagg    900
aagatgacta cgaggagatg taacacaacc gggagatctg accacaggtt cgctcgaggg    960
actttggaag aacgcagaca cttcaat                                        987
```

<210> SEQ ID NO 10
<211> LENGTH: 663
<212> TYPE: DNA
<213> ORGANISM: Drosophila melanogaster

<400> SEQUENCE: 10

```
atgaactttg ccttcaataa taataatccg gatggcgaag gaggcaccgg cgtcgatggt     60
ggcggtggtg gtgctggtgg tggtgccgct ggtcccggcg gtagaaccgg ggattcgccc    120
cattcacaag aaggtgacgg tagtgctgcg acggataacc ccaatgacga ccacgctaca    180
tctgctgata atagtttggc tactgatggc gatgccattg gtaagaagga aagcggcggt    240
ggtagcgatg gcaagagcga ctccaaagac tcgagcggag gcaatgatgc cacgccagcg    300
aatggtcatg acgatgacaa cgatgacagc gacagaagga tgccaaggat cgacaagata    360
aggaagagga ggccggacag gaggggaagc gcaccgatta cagccatcac agtagctacg    420
agatcagatc gacgacagct ttgtgccggc tccaatcagc ggacaatgga gcccgtgaga    480
gcagtcagga gaaccaggat gccaggaag tggccagcga agcgcctgct caacgggcag     540
gcaacgtgcc agatggaccc gaaactggag ccaaggaaga tgactacgag gagatgtaac    600
acaaccggga gatctgacca caggttcgct cgagggactt tggaagaacg cagacacttc    660
aat                                                                 663
```

<210> SEQ ID NO 11
<211> LENGTH: 267
<212> TYPE: PRT
<213> ORGANISM: Drosophila melanogaster

<400> SEQUENCE: 11

Met Pro Pro Leu Leu Arg His Glu Phe Gly His Ala Phe Ile Gly Leu
1               5                   10                  15

Pro Leu Phe Asn Gly Gln Glu Gln Pro Arg Pro Gln Met Asn Phe Ala
            20                  25                  30

Phe Asn Asn Asn Pro Asp Gly Glu Gly Thr Gly Val Asp Gly
        35                  40                  45

Gly Gly Gly Gly Ala Gly Gly Ala Ala Gly Pro Gly Gly Gly Thr
    50                  55                  60

Gly Asp Ser Pro His Ser Gln Glu Gly Asp Gly Ser Ala Ala Thr Asp
65                  70                  75                  80

Asn Pro Asn Asp Asp His Ala Thr Ser Ala Asp Asn Ser Leu Ala Thr
                85                  90                  95

Asp Gly Asp Ala Ile Gly Lys Lys Glu Ser Gly Gly Ser Asp Gly
            100                 105                 110

Lys Ser Asp Ser Lys Asp Ser Ser Gly Gly Asn Asp Ala Thr Pro Ala
        115                 120                 125

Asn Gly His Asp Asp Asp Asn Asp Asp Ser Asp Arg Arg Met Pro Arg
    130                 135                 140

Ile Asp Lys Ile Arg Lys Arg Arg Pro Asp Arg Arg Gly Ser Ala Pro
145                 150                 155                 160

Ile Thr Ala Ile Thr Val Ala Thr Arg Ser Asp Arg Arg Leu Trp Arg
                165                 170                 175

Ala Val Arg Ala Val His Leu Arg Glu Arg Glu Pro Arg Thr Phe Gly
            180                 185                 190

Ser Asn Ala Gly Ser Asn Gln Arg Thr Met Glu Pro Val Arg Ala Val
        195                 200                 205

Arg Arg Thr Arg Met Pro Arg Lys Trp Pro Ala Lys Arg Leu Leu Asn
    210                 215                 220

Gly Gln Ala Thr Cys Gln Met Asp Pro Lys Leu Glu Pro Arg Lys Met
225                 230                 235                 240

Thr Thr Arg Arg Cys Asn Thr Thr Gly Arg Ser Asp His Arg Phe Ala
                245                 250                 255

Arg Gly Thr Leu Glu Glu Arg Arg His Phe Asn
            260                 265

<210> SEQ ID NO 12
<211> LENGTH: 238
<212> TYPE: PRT
<213> ORGANISM: Drosophila melanogaster

<400> SEQUENCE: 12

Met Asn Phe Ala Phe Asn Asn Asn Pro Asp Gly Glu Gly Thr
1               5                   10                  15

Gly Val Asp Gly Gly Gly Gly Gly Ala Gly Gly Ala Ala Gly Pro
            20                  25                  30

Gly Gly Gly Thr Gly Asp Ser Pro His Ser Gln Glu Gly Asp Gly Ser
        35                  40                  45

Ala Ala Thr Asp Asn Pro Asn Asp Asp His Ala Thr Ser Ala Asp Asn
    50                  55                  60

Ser Leu Ala Thr Asp Gly Asp Ala Ile Gly Lys Lys Glu Ser Gly Gly
 65                  70                  75                  80

Gly Ser Asp Gly Lys Ser Asp Ser Lys Asp Ser Ser Gly Gly Asn Asp
                 85                  90                  95

Ala Thr Pro Ala Asn Gly His Asp Asp Asn Asp Asp Ser Asp Arg
            100                 105                 110

Arg Met Pro Arg Ile Asp Lys Ile Arg Lys Arg Pro Asp Arg Arg
        115                 120                 125

Gly Ser Ala Pro Ile Thr Ala Ile Thr Val Ala Thr Arg Ser Asp Arg
    130                 135                 140

Arg Leu Trp Arg Ala Val Arg Ala Val His Leu Arg Glu Arg Glu Pro
145                 150                 155                 160

Arg Thr Glu Gly Ser Asn Ala Gly Ser Asn Gln Arg Thr Met Glu Pro
                165                 170                 175

Val Arg Ala Val Arg Arg Thr Arg Met Pro Arg Lys Trp Pro Ala Lys
            180                 185                 190

Arg Leu Leu Asn Gly Gln Ala Thr Cys Gln Met Asp Pro Lys Leu Glu
        195                 200                 205

Pro Arg Lys Met Thr Thr Arg Arg Cys Asn Thr Thr Gly Arg Ser Asp
210                 215                 220

His Arg Phe Ala Arg Gly Thr Leu Glu Glu Arg Arg His Phe
225                 230                 235

<210> SEQ ID NO 13
<211> LENGTH: 367
<212> TYPE: DNA
<213> ORGANISM: Drosophila melanogaster

<400> SEQUENCE: 13
ggattctaca agatgctacc ttccaagcga gttccatttc ttttcaccat tatcctgttt      60
ctggctggac tgggtcagca cacaactgaa agtgtacttc cagactgcgt tctttatcca     120
agatgtttga tcacaaagga tccgtgttgc atgtaaagca tctatagaaa tcaaagaagg     180
atcttgtata tggaagtgga aatgtggttc aaaatatcag cacttctcaa ggctgtaaca     240
aaaactgcac tctgttttta aaatacaaa tatccacaaa tatctggtct aacatggca      300 acatttcaag tcttccaata aatcattttc gttttattg tgaaaaaaaa aaaaaaaaa      360 aaaaaaa                                                               367

<210> SEQ ID NO 14
<211> LENGTH: 151
<212> TYPE: DNA
<213> ORGANISM: Drosophila melanogaster

<400> SEQUENCE: 14
atgctacctt ccaagcgagt tccatttctt ttcaccatta tcctgtttct ggctggactg      60
ggtcagcaca caactgaaag tgtacttcca gactgcgttc gactgcgttc tttatccaag     120
atgtttgatc acaaaggatc cgtgttgcat g                                    151

<210> SEQ ID NO 15
<211> LENGTH: 129
<212> TYPE: DNA
<213> ORGANISM: Drosophila melanogaster

<400> SEQUENCE: 15
atggaagtgg aaatgtggtt caaaatatca gcacttctca aggctgtaac aaaaactgca      60

```
ctctgttttt ataaatacaa atatccacaa atatctggtc ttaacatggc aacatttcaa     120
gtcttccaa                                                             129
```

<210> SEQ ID NO 16
<211> LENGTH: 47
<212> TYPE: PRT
<213> ORGANISM: Drosophila melanogaster

<400> SEQUENCE: 16

```
Met Leu Pro Ser Lys Arg Val Pro Phe Leu Phe Thr Ile Ile Leu Phe
  1               5                  10                  15

Leu Ala Gly Leu Gly Gln His Thr Thr Glu Ser Val Leu Pro Asp Cys
             20                  25                  30

Val Leu Tyr Pro Arg Cys Leu Ile Thr Lys Asp Pro Cys Cys Met
         35                  40                  45
```

<210> SEQ ID NO 17
<211> LENGTH: 43
<212> TYPE: PRT
<213> ORGANISM: Drosophila melanogaster

<400> SEQUENCE: 17

```
Met Glu Val Glu Met Trp Phe Lys Ile Ser Ala Leu Leu Lys Ala Val
  1               5                  10                  15

Thr Lys Thr Ala Leu Cys Phe Tyr Lys Tyr Lys Tyr Pro Gln Ile Ser
             20                  25                  30

Gly Leu Asn Met Ala Thr Phe Gln Val Phe Gln
         35                  40
```

<210> SEQ ID NO 18
<211> LENGTH: 2492
<212> TYPE: DNA
<213> ORGANISM: Drosophila melanogaster

<400> SEQUENCE: 18

```
caaatcaaca actaattaat gcacaagacg tgctctcaga caaagatcag aaacagacgc      60
aagttcagaa caataactta catattcgat tcggtgtgtc agcactaaga gaaggaagaa     120
ataatcctag tttggaaacg atttctcggg ataaagtaga taaatatcca cctgcattgc     180
agttgcaact gttgagatat gcagattctc agtcgcaatc ccagacgcag tcacaatctg     240
cctcacaatc tgaatcaaat gcatcttcac aattccaggc acaggagcaa agcaatcgac     300
tgttgggaaa acccacctgt ttcagaatct cagtcacaat cagagtcaca gtcacagtcc     360
gagtcacaga agcagtcaca gtcgcagtca cagcgacagc aacagataca gacgcaattg     420
caaatactgc gacagttgca acaaaagtca aatgagcaat ctgccgcaca atctgcttct     480
cagattcaat cgcagaggca atcggattct caatccaact acaattaca  agaacaatca     540 caatcgcagt cagagcaagg taagccaatc cagtcacaaa ttcaaattct tcaagggctg     600
cagcaaaaag agttagatga caaatctgca tcacagtcgc agtccgaatc caagacacgg     660
aaagagcaac aaaaacagtt gaatttgcaa caacttgagg agctatcgtc ttcactatca     720
cagtcacggc tagggctggg acagcaaatc cagtcacagc tacaaaagaa tcagttggat     780
aagcaatttt cttcacagtt tcagtcacaa tccaagtcac agctggagca acaaatgcaa     840
ttgcaattac aaagccttcg gcaactgcag cagaagcaat tagatgagca atctgcttca     900
cagtcgcagc cacagtcaca ggtagcgcaa cagatccagt cacatttgca acttcttcga     960
```

-continued

```
ttactgcaat ccagattgaa gacgcagtcg gcattgaaat cagatttaga acaacaaatc      1020 cttttttcaat taaagaaact tacagaagtg caacagaaac agttggctga gcaacccacc    1080
ttacgaccca gttcaaaatc acaatcgcct gggcagctag agcagcaaat tctgttacac     1140
ctgcaaaatc ttctacactt tcagcagaat cagctaaaat cagatacaca aacccaaagc    1200
cagttgcaag agtcaaaatc taactcactg tcacagtcac agtcacaatc gcaggagcag    1260
ttacagttgc agcgggatca gaatcttcgg caattggaac aagtaaagtt ggaaatgcaa    1320
aatattcgag agctgctgca gaagggcaag tctgagctac aaacccaatc ggactctcag    1380
cgacgtatac atgagctata ccaaaatatt ctgcagctaa ataaggagaa gttgagctac    1440
caattgaaac agtaaaaact aaaagaattg gaagaccaaa agaagtcgca ggcagaaata    1500 tcaagggaa gtaacccatc caatctattt attatcggac aattgccttc cgaaggaaag     1560
ccagctcctg gaaatcaagg tccttcaatt gagcctaagc tggtccccca acccggttca    1620
ctggacaaat tgccatcagg cggagggcta attggcaagc cagcttcaac aggactgtat    1680
attttatcgc cggatttcaa tgatttgtcg gattaccgag atcagtttcg tctacagcaa    1740
gaattaaaaa agcatcaaaa tatattgagc cttttgcagc gtagacaaaa tgataaaaaa    1800
caacaaaacg cacagctgtt gctaggacaa caacagaagg aacaacaagc tcaggaatca    1860
atcaataaac aacagtcctc atctgctggc tctagttctc agaccaagtt acagcaagat    1920
atacaaagta ctggagctca aggctcacag cagggtcttc aagctggatc cactggcctg    1980
cagactagtt ccctacaagg cacagaaagt tctgcatctc aaagcgctct tcagcgattg    2040
aaggagcagg aacaactgcg aattcagacg gaaaatgatc agaaaacctc ttcttcaagc    2100
tcgcacagta actcacaaaa ctcgcagagt tcgtcatcac agtcatcgca ggcatcacag    2160
tctgaagcac aacgacagga ggctggcaat cgaaatacct tgctactaga tcaatcgagc    2220
tccaagactc agtcgagtcg aagtccgagt cgtcgtctca atcatcgtca cattcatcgt    2280
cgcagtcaac gtcgaactca tcttcaaacg ttcaatcgaa actacaagga gaaagccaag    2340
cgctgctaaa caatttgtca ggttaagtag ttaaccttat acttctcaca gtactgacat    2400
gggcgaagag cagccttatt cagatgttaa tcaaaagag gaaataaaat aattgttctt    2460
tcatttaaaa actcgaaaaa aaaaaaaaaa aa                                    2492
```

<210> SEQ ID NO 19
<211> LENGTH: 2148
<212> TYPE: DNA
<213> ORGANISM: Drosophila melanogaster

<400> SEQUENCE: 19

```
atgcagattc tcagtcgcaa tcccagacgc agtcacaatc tgcctcacaa tctgaatcaa      60
atgcatcttc acaattccag gcacaggagc aaagcaatcg actgttggga aaacccacct    120
gtttcagaat ctcagtcaca atcagagtca cagtcacagt ccgagtcaca gaagcagtca    180
cagtcgcagt cacagcgaca gcaacagata cagacgcaat tgcaaatact gcgacagttg    240
caacaaaagt caaatgagca atctgccgca caatctgctt tcagattca atcgcagagg    300 caatcggatt ctcaatccaa cttacaatta caagaacaat cacaatcgca gtcagagcaa    360
ggtaagccaa tccagtcaca aattcaaatt cttcaagggc tgcagcaaaa agagttagat    420
gacaaatctg catcacagtc gcagtccgaa tccaagacac ggaaagagca acaaaaacag    480
ttgaatttgc aacaacttga ggagctatcg tcttcactat cacagtcacg gctagggctg    540
ggacagcaaa tccagtcaca gctacaaaag aatcagttgg ataagcaatt ttcttcacag    600
```

-continued

```
tttcagtcac aatccaagtc acagctggag caacaaatgc aattgcaatt acaaagcctt      660
cggcaactgc agcagaagca attagatgag caatctgctt cacagtcgca gccacagtca      720
caggtagcgc aacagatcca gtcacatttg caacttcttc gattactgca atccagattg      780
aagacgcagt cggcattgaa atcagattta aacaacaaa tccttttca attaaagaaa       840 cttacagaag tgcaacagaa acagttggct gagcaaccca ccttacgacc cagttcaaaa      900
tcacaatcgc ctgggcagct agagcagcaa attctgttac acctgcaaaa tcttctacac      960
tttcagcaga atcagctaaa atcagataca caaacccaaa gccagttgca agagtcaaaa     1020
tctaactcac tgtcacagtc acagtcacaa tcgcaggagc agttacagtt gcagcgggat     1080
cagaatcttc ggcaattgga acaagtaaag ttggaaatgc aaaatattcg agagctgctg     1140
cagaagggca agtctgagct acaaacccaa tcggactctc agcgacgtat acatgagcta     1200
taccaaaata ttctgcagct aaataaggag aagttgagct accaattgaa acagttaaaa     1260
ctaaaagaat tggaagacca aaagaagtcg caggcagaaa tatcaaaggg aagtaaccca     1320
tccaatctat ttattatcgg acaattgcct tccgaaggaa agccagctcc tggaaatcaa     1380
ggtccttcaa ttgagcctaa gctggtcccc caacccggtt cactggacaa attgccatca     1440
ggcggagggc taattggcaa gccagcttca acaggactgt atattttatc gccggatttc     1500
aatgatttgt cggattaccg agatcagttt cgtctacagc aagaattaaa aaagcatcaa     1560
aatatattga gccttttgca gcgtagacaa aatgataaaa acaacaaaa cgcacagctg     1620 ttgctaggac aacaacagaa ggaacaacaa gctcaggaat caatcaataa acaacagtcc     1680
tcatctgctg gctctagttc tcagaccaag ttacagcaag atatacaaag tactggagct     1740
caaggctcac agcagggtct tcaagctgga tccactggcc tgcagactag ttccctacaa     1800
ggcacagaaa gttctgcatc tcaaagcgct cttcagcgat tgaaggagca ggaacaactg     1860
cgaattcaga cggaaaatga tcagaaaacc tcttcttcaa gctcgcacag taactcacaa     1920
aactcgcaga gttcgtcatc acagtcatcg caggcatcac agtctgaagc acaacgacag     1980
gaggctggca atcgaaatac cttgctacta gatcaatcga gctccaagac tcagtcgagt     2040
cgaagtccga gtcgtcgtct caatcatcgt cacattcatc gtcgcagtca acgtcgaact     2100
catcttcaaa cgttcaatcg aaactacaag gagaaagcca agcgctgc                  2148
```

<210> SEQ ID NO 20
<211> LENGTH: 716
<212> TYPE: PRT
<213> ORGANISM: Drosophila melanogaster

<400> SEQUENCE: 20

```
Met Gln Ile Leu Ser Arg Asn Pro Arg Arg Ser His Asn Leu Pro His
  1               5                  10                  15

Asn Leu Asn Gln Met His Leu His Asn Ser Arg His Arg Ser Lys Ala
             20                  25                  30

Ile Asp Cys Trp Glu Asn Pro Val Ser Glu Ser Gln Ser Gln Ser
         35                  40                  45

Glu Ser Gln Ser Gln Ser Glu Ser Gln Lys Gln Ser Gln Ser Gln Ser
     50                  55                  60

Gln Arg Gln Gln Gln Ile Gln Thr Gln Leu Gln Ile Leu Arg Gln Leu
 65                  70                  75                  80

Gln Gln Lys Ser Asn Glu Gln Ser Ala Ala Gln Ser Ala Ser Gln Ile
                 85                  90                  95
```

-continued

```
Gln Ser Gln Arg Gln Ser Asp Ser Gln Ser Asn Leu Gln Leu Gln Glu
                100                 105                 110

Gln Ser Gln Ser Gln Ser Glu Gln Gly Lys Pro Ile Gln Ser Gln Ile
            115                 120                 125

Gln Ile Leu Gln Gly Leu Gln Gln Lys Glu Leu Asp Asp Lys Ser Ala
        130                 135                 140

Ser Gln Ser Gln Ser Glu Ser Lys Thr Arg Lys Glu Gln Gln Lys Gln
145                 150                 155                 160

Leu Asn Leu Gln Gln Leu Glu Glu Leu Ser Ser Leu Ser Gln Ser
                165                 170                 175

Arg Leu Gly Leu Gly Gln Gln Ile Gln Ser Gln Leu Gln Lys Asn Gln
                180                 185                 190

Leu Asp Lys Gln Phe Ser Ser Gln Phe Gln Ser Gln Ser Lys Ser Gln
            195                 200                 205

Leu Glu Gln Gln Met Gln Leu Gln Leu Gln Ser Leu Arg Gln Leu Gln
        210                 215                 220

Gln Lys Gln Leu Asp Glu Gln Ser Ala Ser Gln Ser Gln Pro Gln Ser
225                 230                 235                 240

Gln Val Ala Gln Gln Ile Gln Ser His Leu Gln Leu Leu Arg Leu Leu
                245                 250                 255

Gln Ser Arg Leu Lys Thr Gln Ser Ala Leu Lys Ser Asp Leu Glu Gln
                260                 265                 270

Gln Ile Leu Phe Gln Leu Lys Lys Leu Thr Glu Val Gln Gln Lys Gln
        275                 280                 285

Leu Ala Glu Gln Pro Thr Leu Arg Pro Ser Ser Lys Ser Gln Ser Pro
        290                 295                 300

Gly Gln Leu Glu Gln Gln Ile Leu Leu His Leu Gln Asn Leu Leu His
305                 310                 315                 320

Phe Gln Gln Asn Gln Leu Lys Ser Asp Thr Gln Thr Gln Ser Gln Leu
                325                 330                 335

Gln Glu Ser Lys Ser Asn Ser Leu Ser Gln Ser Gln Ser Gln Ser Gln
                340                 345                 350

Glu Gln Leu Gln Leu Gln Arg Asp Gln Asn Leu Arg Gln Leu Glu Gln
        355                 360                 365

Val Lys Leu Glu Met Gln Asn Ile Arg Glu Leu Leu Gln Lys Gly Lys
        370                 375                 380

Ser Glu Leu Gln Thr Gln Ser Asp Ser Gln Arg Arg Ile His Glu Leu
385                 390                 395                 400

Tyr Gln Asn Ile Leu Gln Leu Asn Lys Glu Lys Leu Ser Tyr Gln Leu
                405                 410                 415

Lys Gln Leu Lys Leu Lys Glu Leu Glu Asp Gln Lys Lys Ser Gln Ala
            420                 425                 430

Glu Ile Ser Lys Gly Ser Asn Pro Ser Asn Leu Phe Ile Ile Gly Gln
        435                 440                 445

Leu Pro Ser Glu Gly Lys Pro Ala Pro Gly Asn Gln Gly Pro Ser Ile
        450                 455                 460

Glu Pro Lys Leu Val Pro Gln Pro Gly Ser Leu Asp Lys Leu Pro Ser
465                 470                 475                 480

Gly Gly Gly Leu Ile Gly Lys Pro Ala Ser Thr Gly Leu Tyr Ile Leu
                485                 490                 495

Ser Pro Asp Phe Asn Asp Leu Ser Asp Tyr Arg Asp Gln Phe Arg Leu
                500                 505                 510

Gln Gln Glu Leu Lys Lys His Gln Asn Ile Leu Ser Leu Leu Gln Arg
```

```
                515                 520                 525
Arg Gln Asn Asp Lys Lys Gln Gln Asn Ala Gln Leu Leu Leu Gly Gln
            530                 535                 540

Gln Gln Lys Glu Gln Gln Ala Gln Glu Ser Ile Asn Lys Gln Gln Ser
545                 550                 555                 560

Ser Ser Ala Gly Ser Ser Gln Thr Lys Leu Gln Gln Asp Ile Gln
                565                 570                 575

Ser Thr Gly Ala Gln Gly Ser Gln Gln Gly Leu Gln Ala Gly Ser Thr
            580                 585                 590

Gly Leu Gln Thr Ser Ser Leu Gln Gly Thr Glu Ser Ser Ala Ser Gln
        595                 600                 605

Ser Ala Leu Gln Arg Leu Lys Glu Gln Glu Gln Leu Arg Ile Gln Thr
    610                 615                 620

Glu Asn Asp Gln Lys Thr Ser Ser Ser Ser His Ser Asn Ser Gln
625                 630                 635                 640

Asn Ser Gln Ser Ser Ser Ser Gln Ser Ser Gln Ala Ser Gln Ser Glu
                645                 650                 655

Ala Gln Arg Gln Glu Ala Gly Asn Arg Asn Thr Leu Leu Leu Asp Gln
            660                 665                 670

Ser Ser Ser Lys Thr Gln Ser Ser Arg Ser Pro Ser Arg Arg Leu Asn
        675                 680                 685

His Arg His Ile His Arg Arg Ser Gln Arg Arg Thr His Leu Gln Thr
    690                 695                 700

Phe Asn Arg Asn Tyr Lys Glu Lys Ala Lys Arg Cys
705                 710                 715
```

<210> SEQ ID NO 21
<211> LENGTH: 440
<212> TYPE: DNA
<213> ORGANISM: Drosophila melanogaster

<400> SEQUENCE: 21

```
ccgaaagcac acagataagg cttccaatga aactgataaa ggttacacta gtgttcagct    60
tactggctct cgtatttgtg gcccaaacgg aggcgcaaaa tccaatatgg gagaattggc   120
tggcatgcaa tagaattggt actaaagcgc ttgccagtct gctgagagaa acaattccaa   180
ccgttcgtaa tttactgaac tgcattgact tcaatccacc aaccgatatt ggaaatagtt   240
acctttcaaa acttaagtta tactatgagc ttgttaagcg aggtgcgctt gacaagactc   300
agtgtctgat tgtgccactc aaggaatcag tgagactact gaggccttat gtaaaatcgc   360
ttgagaccaa caaatgcttg ggtgaataaa tcactatttt ggccatagta aaataaattt   420
ctgagcatta ataaagcacg                                               440
```

<210> SEQ ID NO 22
<211> LENGTH: 360
<212> TYPE: DNA
<213> ORGANISM: Drosophila melanogaster

<400> SEQUENCE: 22

```
atgaaactga taaggttac actagtgttc agcttactgg ctctcgtatt tgtgcccaa     60
acggaggcgc aaaatccaat atgggagaat tggctggcat gcaatagaat tggtactaaa   120
gcgcttgcca gtctgctgag agaaacaatt ccaaccgttc gtaatttact gaactgcatt   180
gacttcaatc caccaaccga tattggaaat agttaccttt caaaacttaa gttatactat   240
gagcttgtta agcgaggtgc gcttgacaag actcagtgtc tgattgtgcc actcaaggaa   300
```

-continued tcagtgagac tactgaggcc ttatgtaaaa tcgcttgaga ccaacaaatg cttgggtgaa    360

<210> SEQ ID NO 23
<211> LENGTH: 120
<212> TYPE: PRT
<213> ORGANISM: Drosophila melanogaster

<400> SEQUENCE: 23

Met Lys Leu Ile Lys Val Thr Leu Val Phe Ser Leu Leu Ala Leu Val
 1               5                  10                  15

Phe Val Ala Gln Thr Glu Ala Gln Asn Pro Ile Trp Glu Asn Trp Leu
            20                  25                  30

Ala Cys Asn Arg Ile Gly Thr Lys Ala Leu Ala Ser Leu Leu Arg Glu
        35                  40                  45

Thr Ile Pro Thr Val Arg Asn Leu Leu Asn Cys Ile Asp Phe Asn Pro
    50                  55                  60

Pro Thr Asp Ile Gly Asn Ser Tyr Leu Ser Lys Leu Lys Leu Tyr Tyr
65                  70                  75                  80

Glu Leu Val Lys Arg Gly Ala Leu Asp Lys Thr Gln Cys Leu Ile Val
                85                  90                  95

Pro Leu Lys Glu Ser Val Arg Leu Leu Arg Pro Tyr Val Lys Ser Leu
            100                 105                 110

Glu Thr Asn Lys Cys Leu Gly Glu
        115                 120

<210> SEQ ID NO 24
<211> LENGTH: 323
<212> TYPE: DNA
<213> ORGANISM: Drosophila melanogaster

<400> SEQUENCE: 24
ctttgcaaga tgaaagctat catcgttttt attctgttca tttcaagtgt gcatgctatg    60
agcaaatgca accaagcaat ttatctaaat cttgatcctc actgcggaat acttcccgat   120
tgtaacttag atggtccaaa tccaagttac ctcaataggg tgtcgtgtga acgcaaagaa   180
aacggaaaac caggattcat cgaactaatt cccggaaaat gtctccatgg taaaccgcgt   240
tgctcgttaa atagtaata ttgttccaat atttccatgc atatatgttt caattaaagg   300
cattataaat acctataaaa aaa                                           323

<210> SEQ ID NO 25
<211> LENGTH: 243
<212> TYPE: DNA
<213> ORGANISM: Drosophila melanogaster

<400> SEQUENCE: 25
atgaaagcta tcatcgtttt tattctgttc atttcaagtg tgcatgctat gagcaaatgc    60
aaccaagcaa tttatctaaa tcttgatcct cactgcggaa tacttcccga ttgtaactta   120
gatggtccaa atccaagtta cctcaatagg gtgtcgtgtg aacgcaaaga aaacggaaaa   180
ccaggattca tcgaactaat tcccggaaaa tgtctccatg gtaaaccgcg ttgctcgtta   240
aaa                                                                 243

<210> SEQ ID NO 26
<211> LENGTH: 81
<212> TYPE: PRT
<213> ORGANISM: Drosophila melanogaster

<400> SEQUENCE: 26

| Met | Lys | Ala | Ile | Ile | Val | Phe | Ile | Leu | Phe | Ile | Ser | Ser | Val | His | Ala |
| 1 | | | | 5 | | | | | 10 | | | | | 15 | |
| Met | Ser | Lys | Cys | Asn | Gln | Ala | Ile | Tyr | Leu | Asn | Leu | Asp | Pro | His | Cys |
| | | | 20 | | | | | 25 | | | | | 30 | | |
| Gly | Ile | Leu | Pro | Asp | Cys | Asn | Leu | Asp | Gly | Pro | Asn | Pro | Ser | Tyr | Leu |
| | | | 35 | | | | | 40 | | | | | 45 | | |
| Asn | Arg | Val | Ser | Cys | Glu | Arg | Lys | Glu | Asn | Gly | Lys | Pro | Gly | Phe | Ile |
| | 50 | | | | | 55 | | | | | 60 | | | | |
| Glu | Leu | Ile | Pro | Gly | Lys | Cys | Leu | His | Gly | Lys | Pro | Arg | Cys | Ser | Leu |
| 65 | | | | | 70 | | | | | 75 | | | | | 80 |
| Lys | | | | | | | | | | | | | | | |

<210> SEQ ID NO 27
<211> LENGTH: 2092
<212> TYPE: DNA
<213> ORGANISM: Drosophila melanogaster

<400> SEQUENCE: 27

| atatcaagct tatgactctt ggataagcca ttgatatagc aattgtaaat atattatgtg | 60 |
| caattctcct tattttctaa gacattctta ataatataat gcgaactaag gttacattcc | 120 |
| atctgcgcat gcgtgagtcc ttttgctcag caggaacgaa agtacaacgg tcgtatgag | 180 |
| ttatggcaat cgaatgggca cacgtggccg ccggtccaat ggccagtaaa tcaaactttt | 240 |
| tggcagggcg agtaaacagt gttataaatc agaaaaccgc aaggcagcca ccaggcagct | 300 |
| accatattgt ccatggagga aagcagacag ttggcagact taagtcggac gaaaagacat | 360 |
| ccacccacgc gggcggattg caatgtgcca ggatgcaagt gacgcatagt gctattaaca | 420 |
| tattaccagg cggtaagtgg gtggataaca cattcagtcg gtggatggaa gtacgtgcat | 480 |
| agaacataga gctgccagtg aatattggag caattggagc actgggtgct aaatatgagc | 540 |
| acttgatgaa aacataacac tgactaaaca agatatttct ctgcggctga atttatctag | 600 |
| cgaaagtgtg aaattgttgt tgatttatgt tatactaagc acgccatata tatgaggtgg | 660 |
| cgaatttacg acgatttact aagattttaa tgtactcttc cttggttaga ggatagaaag | 720 |
| catgaaattg aatagcagtg caataaatcc gtactaattt ccattcgttt ttgcgtatta | 780 |
| tccaatatct taagggtcat tccccttgtg tgtatatata ggaacaaagt aagtttaaga | 840 |
| agctcattgc ggctttggaa aatgggcaac catcaagtaa cattcttagt actgtgcacg | 900 |
| tcgctcctct ttcaaaatac aatacaacaa aatgtatcat ttcaactgat aagggaaatc | 960 |
| gatagataca caccagagaa ttttgtacta tcagtgttga atatagaaat gattcttttt | 1020 |
| gagatccatg ccgctaaggc agttgaaagt aataacgatt tggaaaggag cttgatcata | 1080 |
| aactttggat actccgaagc aaggcaggaa gtactggatt ggggattgag atataagaaa | 1140 |
| gcctcgagcg ccaagttcca gatggccaac aaggtggcag tgtctcagaa actgccccta | 1200 |
| tcgcaaaagc tgcgtctggt aaacgaggtg ctgatgacga gcgccaagaa gtatgatgta | 1260 |
| acaaaggatg tcagaccatc aaaattaatg gatgaatggt tgtcctccca tttggatggt | 1320 |
| gtactcgcca atttgtaca agagaagaag ttaaacgcgg gcgaaaacat tgtagccatc | 1380 |
| agcggaatga cagtcactcc cctttgggca tctcatttcc aatcagagat taatagatac | 1440 |
| tttgtcaata atcctggcac tggatatgct tcgaaagacc caacatgtgt gcccatgatg | 1500 |
| cactcattgt cctcgtttga aaccatgtcc acggacgagg ccaaaggtat atacattcca | 1560 |

| | |
|---|---|
| ttctcatcgg caaacttggg tatgttgatc ctcctgccga ggaaaggtgt cacctgcaag | 1620 |
| gacattttgg ataatttaaa caaccagatc aatgtggaat ataatgatca caaggatgtt | 1680 |
| cacttgctac tgcccatatt caaggagaaa tttgactaca atattgccaa attctttaac | 1740 |
| ggaattaaca ttgaagacac gtttaaagat tcggcgttta atcgaaagc caaaatcaaa | 1800 |
| atcaacaact tccgagtcaa ccatggcata cgatttcaac ccattctccg tttagaagta | 1860 |
| gttgatgata ttaatactgg aaagaccgaa acgtttgaag taaatcgccc atttgtcttt | 1920 |
| gtcataaagg ataaggttaa cgtatacgca gttggtcgaa ttgaaaacct agatggactt | 1980 |
| actgacaaag tgaattgctc caagaaatac gctgatctca gtcgtaaaa tatccataat | 2040 |
| atatttcgaa gcataataaa gcaagaaaat ataaaaaaaa aaaaaaaaaa aa | 2092 |

<210> SEQ ID NO 28
<211> LENGTH: 1164
<212> TYPE: DNA
<213> ORGANISM: Drosophila melanogaster

<400> SEQUENCE: 28

| | |
|---|---|
| atgggcaacc atcaagtaac attcttagta ctgtgcacgt cgctcctctt tcaaaataca | 60 |
| atacaacaaa atgtatcatt tcaactgata agggaaatcg atagatacac accagagaat | 120 |
| tttgtactat cagtgttgaa tatagaaatg attcttttg agatccatgc cgctaaggca | 180 |
| gttgaaagta ataacgattt ggaaaggagc ttgatcataa actttggata ctccgaagca | 240 |
| aggcaggaag tactggattg gggattgaga tataagaaag cctcgagcgc caagttccag | 300 |
| atggccaaca aggtggcagt gtctcagaaa ctgcccctat cgcaaaagct gcgtctggta | 360 |
| aacgaggtgc tgatgacgag cgccaagaag tatgatgtaa caaggatgt cagaccatca | 420 |
| aaattaatgg atgaatggtt gtcctcccat ttggatggtg tactcgccaa ttttgtacaa | 480 |
| gagaagaagt taaacgcggg cgaaaacatt gtagccatca gcggaatgac agtcactccc | 540 |
| ctttgggcat ctcatttcca atcagagatt aatagatact tgtcaataa tcctggcact | 600 |
| ggatatgctt cgaaagaccc aacatgtgtg cccatgatgc actcattgtc ctcgtttgaa | 660 |
| accatgtcca cggacgaggc caaggtatta cattccat tctcatcggc aaacttgggt | 720 |
| atgttgatcc tcctgccgag gaaaggtgtc acctgcaagg acattttgga taatttaaac | 780 |
| aaccagatca atgtggaata taatgatcac aaggatgttc acttgctact gcccatattc | 840 |
| aaggagaaat ttgactacaa tattgccaaa ttctttaacg gaattaacat tgaagacacg | 900 |
| tttaaagatt cggcgtttaa atcgaaagcc aaaatcaaaa tcaacaactt ccgagtcaac | 960 |
| catggcatac gatttcaacc cattctccgt ttagaagtag ttgatgatat taatactgga | 1020 |
| aagaccgaaa cgtttgaagt aaatcgccca tttgtctttg tcataaagga taaggttaac | 1080 |
| gtatacgcag ttggtcgaat tgaaaaccta gatggactta ctgacaaagt gaattgctcc | 1140 |
| aagaaatacg ctgatctcaa gtcg | 1164 |

<210> SEQ ID NO 29
<211> LENGTH: 388
<212> TYPE: PRT
<213> ORGANISM: Drosophila melanogaster

<400> SEQUENCE: 29

Met Gly Asn His Gln Val Thr Phe Leu Val Leu Cys Thr Ser Leu Leu
1               5                   10                  15

Phe Gln Asn Thr Ile Gln Gln Asn Val Ser Phe Gln Leu Ile Arg Glu
            20                  25                  30

```
Ile Asp Arg Tyr Thr Pro Glu Asn Phe Val Leu Ser Val Leu Asn Ile
         35                  40                  45
Glu Met Ile Leu Phe Glu Ile His Ala Ala Lys Ala Val Glu Ser Asn
 50                  55                  60
Asn Asp Leu Glu Arg Ser Leu Ile Ile Asn Phe Gly Tyr Ser Glu Ala
 65                  70                  75                  80
Arg Gln Glu Val Leu Asp Trp Gly Leu Arg Tyr Lys Lys Ala Ser Ser
                 85                  90                  95
Ala Lys Phe Gln Met Ala Asn Lys Val Ala Val Ser Gln Lys Leu Pro
            100                 105                 110
Leu Ser Gln Lys Leu Arg Leu Val Asn Glu Val Leu Met Thr Ser Ala
            115                 120                 125
Lys Lys Tyr Asp Val Thr Lys Asp Val Arg Pro Ser Lys Leu Met Asp
        130                 135                 140
Glu Trp Leu Ser Ser His Leu Asp Gly Val Leu Ala Asn Phe Val Gln
145                 150                 155                 160
Glu Lys Lys Leu Asn Ala Gly Glu Asn Ile Val Ala Ile Ser Gly Met
                165                 170                 175
Thr Val Thr Pro Leu Trp Ala Ser His Phe Gln Ser Glu Ile Asn Arg
            180                 185                 190
Tyr Phe Val Asn Asn Pro Gly Thr Gly Tyr Ala Ser Lys Asp Pro Thr
            195                 200                 205
Cys Val Pro Met Met His Ser Leu Ser Ser Phe Glu Thr Met Ser Thr
        210                 215                 220
Asp Glu Ala Lys Gly Ile Tyr Ile Pro Phe Ser Ser Ala Asn Leu Gly
225                 230                 235                 240
Met Leu Ile Leu Leu Pro Arg Lys Gly Val Thr Cys Lys Asp Ile Leu
                245                 250                 255
Asp Asn Leu Asn Asn Gln Ile Asn Val Glu Tyr Asn Asp His Lys Asp
            260                 265                 270
Val His Leu Leu Leu Pro Ile Phe Lys Glu Lys Phe Asp Tyr Asn Ile
            275                 280                 285
Ala Lys Phe Phe Asn Gly Ile Asn Ile Glu Asp Thr Phe Lys Asp Ser
        290                 295                 300
Ala Phe Lys Ser Lys Ala Lys Ile Lys Ile Asn Asn Phe Arg Val Asn
305                 310                 315                 320
His Gly Ile Arg Phe Gln Pro Ile Leu Arg Leu Glu Val Val Asp Asp
                325                 330                 335
Ile Asn Thr Gly Lys Thr Glu Thr Phe Glu Val Asn Arg Pro Phe Val
            340                 345                 350
Phe Val Ile Lys Asp Lys Val Asn Val Tyr Ala Val Gly Arg Ile Glu
        355                 360                 365
Asn Leu Asp Gly Leu Thr Asp Lys Val Asn Cys Ser Lys Lys Tyr Ala
        370                 375                 380
Asp Leu Lys Ser
385

<210> SEQ ID NO 30
<211> LENGTH: 163
<212> TYPE: DNA
<213> ORGANISM: Drosophila melanogaster

<400> SEQUENCE: 30
atggaattcc ctaatcctgt tcttagaaga gcagcaggac attccgaacg gaaaggctac      60
```

```
acacactatc aaaggatgac gaggatgtcc aagtgaatca ccagctaaag caaggatatt    120
atgtatatct aaggaaatca aataaacttg catgctctaa aaa                     163
```

<210> SEQ ID NO 31
<211> LENGTH: 93
<212> TYPE: DNA
<213> ORGANISM: Drosophila melanogaster

<400> SEQUENCE: 31

```
atggaattcc ctaatcctgt tcttagccgc attgggcgca gcctccgcac gaataagggg    60
acacactatc aaaggatgac gaggatgtcc aag                                 93
```

<210> SEQ ID NO 32
<211> LENGTH: 31
<212> TYPE: PRT
<213> ORGANISM: Drosophila melanogaster

<400> SEQUENCE: 32

```
Met Glu Phe Pro Asn Pro Val Leu Ser Arg Ile Gly Arg Ser Leu Arg
  1               5                  10                  15

Thr Asn Lys Gly Thr His Tyr Gln Arg Met Thr Arg Met Ser Lys
             20                  25                  30
```

<210> SEQ ID NO 33
<211> LENGTH: 11
<212> TYPE: PRT
<213> ORGANISM: Drosophila melanogaster

<400> SEQUENCE: 33

```
Phe Glu Val Asn Arg Pro Phe Val Phe Val Ile
  1               5                  10
```

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Consensus
      Serpin Signature Sequence
<221> NAME/KEY: UNSURE
<222> LOCATION: (1)
<223> OTHER INFORMATION: X at position 1 is selected from L, I, V, M,
      or F
<221> NAME/KEY: UNSURE
<222> LOCATION: (3)
<223> OTHER INFORMATION: X at position 3 is selected from L, I, V, M, F,
      or A
<221> NAME/KEY: UNSURE
<222> LOCATION: (4)
<223> OTHER INFORMATION: X at position 4 is selected form D, N, or Q
<221> NAME/KEY: UNSURE
<222> LOCATION: (5)
<223> OTHER INFORMATION: X at position 5 is selected from R, K, H, or Q
<221> NAME/KEY: UNSURE
<222> LOCATION: (6)
<223> OTHER INFORMATION: X at position 6 is selected from P or S
<221> NAME/KEY: UNSURE
<222> LOCATION: (8)
<223> OTHER INFORMATION: X at position 8 is selected from L, I, V, M, F,
      or Y
<221> NAME/KEY: UNSURE
<222> LOCATION: (11)
<223> OTHER INFORMATION: X at position 11 is selected from L, I, V, M,
      or F

<400> SEQUENCE: 34

Xaa Xaa Xaa Xaa Xaa Xaa Phe Xaa Xaa Xaa Xaa

```
<210> SEQ ID NO 35
<211> LENGTH: 27
<212> TYPE: PRT
<213> ORGANISM: Phoneutria nigriventer

<400> SEQUENCE: 35

Pro Cys Lys Glu Thr Cys Asp Cys Cys Gly Glu Arg Gly Glu Cys Val
 1               5                  10                  15

Cys Gly Gly Pro Cys Ile Cys Arg Gln Gly Tyr
            20                  25
```